(12) United States Patent
Li et al.

(10) Patent No.: US 9,945,780 B2
(45) Date of Patent: Apr. 17, 2018

(54) USE OF A FLUORESCENT MATERIAL TO DETECT FAILURE OR DETERIORATED PERFORMANCE OF A FLUOROMETER

(71) Applicant: GEN-PROBE INCORPORATED, San Diego, CA (US)

(72) Inventors: Haitao Li, San Diego, CA (US); David Opalsky, San Diego, CA (US); R. Eric Heinz, San Diego, CA (US); Norbert D. Hagen, Carlsbad, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 1259 days.

(21) Appl. No.: 13/912,525

(22) Filed: Jun. 7, 2013

(65) Prior Publication Data
US 2013/0344613 A1    Dec. 26, 2013

Related U.S. Application Data

(60) Provisional application No. 61/659,590, filed on Jun. 14, 2012.

(51) Int. Cl.
*G01N 21/63* (2006.01)
*G01N 21/64* (2006.01)
(Continued)

(52) U.S. Cl.
CPC ......... *G01N 21/645* (2013.01); *G01N 21/276* (2013.01)

(58) Field of Classification Search
CPC .... G01N 21/645; G01N 21/636; G01N 21/63; G01N 21/62; G01N 21/276; G01N 21/274; G01N 21/27; G01N 21/25; G01N 21/17
(Continued)

(56) References Cited

U.S. PATENT DOCUMENTS 3,973,129 A    8/1976 Blumberg et al.
4,302,678 A    11/1981 Schiffert
(Continued)

FOREIGN PATENT DOCUMENTS

CN    1588006 A    3/2005
JP    2011-064526    3/2011
(Continued)

OTHER PUBLICATIONS

International Search Report, International Application No. PCT/US2013/044768, dated Oct. 7, 2013.
(Continued)

*Primary Examiner* — Christine T Mui
(74) *Attorney, Agent, or Firm* — Charles B. Cappellari

(57) ABSTRACT

A System and method for self-checking a fluorometer for failure or deteriorated performance includes fluorescent reference standards mounted on a support to move with respect to one or more fixed fluorometers. The intensity of the fluorescent emission of the fluorescent reference standard is initially measured with the fluorometer, and, after a prescribed interval of usage of the fluorometer, a test measurement of the intensity of the fluorescent emission of the fluorescent standard is taken with the fluorometer. The test measurement is compared to the initial measurement, and failure or deteriorated performance of the fluorometer is determined based on a deviation of the test measurement from the initial measurement.

12 Claims, 26 Drawing Sheets

(51) Int. Cl.
*G01N 21/27* (2006.01)
*G01N 21/62* (2006.01)
*G01N 21/25* (2006.01)

(58) Field of Classification Search
USPC ............ 422/82.08, 82.05, 68.1, 50; 250/226, 250/200, 216
See application file for complete search history.

(56) References Cited

U.S. PATENT DOCUMENTS

| | | | |
|---|---|---|---|
| 5,093,234 | A | 3/1992 | Schwartz |
| 5,157,455 | A | 10/1992 | Macri et al. |
| 5,324,635 | A | 6/1994 | Kawase et al. |
| 5,399,491 | A | 3/1995 | Kacian et al. |
| 5,414,258 | A | 5/1995 | Liang |
| 5,414,285 | A | 5/1995 | Liang |
| 5,435,307 | A | 7/1995 | Friauf et al. |
| 5,612,200 | A | 3/1997 | Dattagupta et al. |
| 5,689,110 | A | 11/1997 | Dietz et al. |
| 5,846,701 | A | 12/1998 | Kacian et al. |
| 6,002,482 | A | 12/1999 | Rothfritz et al. |
| 6,066,458 | A | 5/2000 | Haaland et al. |
| 6,157,454 | A | 12/2000 | Wagner et al. |
| 6,187,267 | B1 | 2/2001 | Taylor et al. |
| 6,242,114 | B1 | 6/2001 | Yamasaki et al. |
| 6,262,799 | B1 | 7/2001 | Wardlaw |
| 6,271,920 | B1 | 8/2001 | Macfarlane et al. |
| 6,335,166 | B1 | 1/2002 | Ammann et al. |
| 6,348,965 | B1 | 2/2002 | Palladino et al. |
| 6,361,945 | B1 | 3/2002 | Becker et al. |
| 6,471,916 | B1 | 10/2002 | Noblett |
| 6,583,424 | B2 | 6/2003 | Stanton et al. |
| 6,656,428 | B1 | 12/2003 | Clark et al. |
| 6,740,871 | B1 | 5/2004 | Stanton et al. |
| 6,842,241 | B2 | 1/2005 | Harju et al. |
| 7,072,036 | B2 | 7/2006 | Jones et al. |
| 7,115,232 | B2 | 10/2006 | Hudson |
| 7,115,374 | B2 | 10/2006 | Linnen et al. |
| 7,148,043 | B2 | 12/2006 | Kordunsky et al. |
| 7,163,589 | B2 | 1/2007 | Kaiser |
| 7,262,842 | B2 | 8/2007 | Ermantraut et al. |
| 7,374,885 | B2 | 5/2008 | Becker et al. |
| 7,381,811 | B2 | 6/2008 | Weisburg et al. |
| 7,417,748 | B2 | 8/2008 | Fox et al. |
| 7,523,637 | B2 | 4/2009 | Roth et al. |
| 7,603,072 | B2 | 10/2009 | Yokobori et al. |
| 7,646,507 | B2 | 1/2010 | Ono |
| 7,695,676 | B2 | 4/2010 | Kloepfer et al. |
| 7,742,164 | B1 | 6/2010 | Phillips et al. |
| 7,831,417 | B2 | 11/2010 | Carrick et al. |
| 7,897,337 | B2 | 3/2011 | Macioszek et al. |
| 2001/0007643 | A1 | 7/2001 | Homer et al. |
| 2003/0015668 | A1 | 1/2003 | Montagu |
| 2005/0202491 | A1 | 9/2005 | Nelson et al. |
| 2006/0208199 | A1 | 9/2006 | Gallagher et al. |
| 2007/0243600 | A1 | 10/2007 | Lair et al. |
| 2010/0108873 | A1 | 5/2010 | Schwertner |
| 2010/0279276 | A1 | 11/2010 | Kacian |

FOREIGN PATENT DOCUMENTS

| | | |
|---|---|---|
| JP | 5273118 A | 8/2013 |
| WO | 8907757 A2 | 8/1989 |
| WO | 9905961 A1 | 2/1999 |
| WO | 2006099255 A2 | 9/2006 |

OTHER PUBLICATIONS

Written Opinion, International Application No. PCT/US2013/044768, dated Oct. 7, 2013.

IP Australia Office Action, Australian Patent Application No. 2013202804, dated Mar. 7, 2014.

Al-Soud et al., "Purification and Characterization of PCR-Inhibitory Components in Blood Cells," J. Clin. Microbiol., Feb. 2001, pp. 485-493, vol. 39, No. 2, American Society for Microbiology, Washington D.C., US.

Mahoney et al., "Urine Specimens from Pregnant and Nonpregnant Women Inhibitory to Amplification of Chlamydia trachomatis nucleic Acid by PCR, Ligase Chain Reaction, and Transcription-Mediated Amplification: Identification of urinary Substances Associated with Inhibition and Removal of Inhibitory Activity," J. Clin. Microbiol., Nov. 1998, pp. 3122-3126, vol. 36, No. 11, American Society for Microbiology, Washington D.C., US.

USE OF A FLUORESCENT MATERIAL TO DETECT FAILURE OR DETERIORATED PERFORMANCE OF A FLUOROMETER

CROSS-REFERENCE TO RELATED APPLICATION

This application claims the benefit under 35 U.S.C. §119 (e) of U.S. Provisional Application No. 61/659,590, filed Jun. 14, 2012, the disclosure of which is hereby incorporated by reference.

BACKGROUND

1. Field of the Invention

The present invention relates to systems and methods for detecting failure or deteriorated performance of an optical signal detector, such as a fluorometer, and, in particular, systems and methods employing fluorescent materials carried on an instrument within which the fluorometer is employed to detect fluorescent signals emitted by sample materials.

2. Background of the Invention

None of the references described or referred to herein are admitted to be prior art to the claimed invention.

Diagnostic assays are widely used in clinical diagnosis and health science research to detect or quantify the presence or amount of biological antigens, cell abnormalities, disease states, and disease-associated pathogens, including parasites, fungi, bacteria and viruses present in a host organism or sample. Where a diagnostic assay permits quantification, practitioners may be better able to calculate the extent of infection or disease and to determine the state of a disease over time. Diagnostic assays are frequently focused on the detection of chemicals, proteins, polysaccharides, nucleic acids, biopolymers, cells, or tissue of interest. A variety of assays may be employed to detect these diagnostic indicators.

Detection of a targeted nucleic acid sequence frequently requires the use of a probe having a nucleotide base sequence that is substantially complementary to the targeted sequence or its amplicon. Under selective assay conditions, the probe will hybridize to the targeted sequence or its amplicon in a manner permitting a practitioner to detect the presence of the targeted sequence in a sample. Probes may include, for example, a label capable of detection, where the label is, for example, a radiolabel, a fluorophore or fluorescent dye, biotin, an enzyme or a chemiluminescent compound.

Because the probe hybridizes to the targeted sequence or its amplicon in a manner permitting detection of a signal indicating the presence of the targeted sequence in a sample, the strength of the signal is proportional to the amount of target sequence or its amplicon that is present. Accordingly, by periodically measuring, during the amplification process, a signal indicative of the presence of amplicon, the growth of amplicon overtime can be detected. Based on the data collected during this "real-time" monitoring of the amplification process, the amount of the target nucleic acid that was originally in the sample can be ascertained. To detect different nucleic acids of interest in a single assay, different probes configured to hybridize to different nucleic acids and to emit detectibly different signals can be used. For example, different probes configured to hybridize to different targets can be formulated with fluorophores that fluoresce at a predetermined wavelength (i.e., color) when exposed to excitation light of a prescribed excitation wavelength. Assays for detecting different target nucleic acids can be performed in parallel by alternately exposing the sample material to different excitation wavelengths and detecting the level of fluorescence at the wavelength of interest corresponding to the probe for each target nucleic acid during the real-time monitoring process. Parallel processing can be performed using different signal detecting devices constructed and arranged to periodically measure signal emissions during the amplification process, and with different signal detecting devices being configured to generate excitation signals of different wavelengths and to measure emission signals of different wavelengths. Suitable signal detecting devices include fluorometers, such as the fluorometer described below. One embodiment of an automated nucleic acid diagnostic instrument is configured to process numerous samples carried in multiple receptacles, and each fluorometer is configured to take fluorometric readings from the receptacles as they are indexed past the fluorometer, for example, once every 2 seconds. Thus, 1800 times for each hour of operation of the instrument, each fluorometer generates an excitation signal that is directed at the sample receptacle and measures the emission signal emitted by the contents of the receptacle, generating an electrical signal that is proportional to the intensity of the emission signal. A malfunction (device failure and/or deteriorated performance) by a fluorometer during operation of the instrument will cause errors in the fluorometric readings generated by that fluorometer and thereby cause errors in the diagnostic results. Such malfunctions may be due to mechanical and/or electrical failures that occur during operation of the fluorometer. While the operation of the fluorometers can be checked during routine maintenance of the instrument, such opportunities for testing are rare, since the testing can only be performed when the instrument is shut down. Ideally, the instrument is operated continuously for extended periods of time for maximum throughput. Therefore, it becomes impractical and non-cost-effective to repeatedly shut the instrument down to perform fluorometer functionality testing. Accordingly, a need exists for means and methodologies for periodically confirming the proper functionality of the fluorometers during the operation of the nucleic acid diagnostic instrument.

SUMMARY OF THE INVENTION

The present invention provides systems and methods for self-checking an optical signal detector, such as a fluorometer, to detect failure or deteriorated performance of the signal detector, wherein self-checking can be performed during normal use of the detector in a dynamic instrument in which the detector is employed and without requiring that the detector be removed from the instrument or that operation of the instrument be interrupted.

Aspects of the invention are embodied in a system for monitoring the performance of a fluorometer in a dynamic environment. The system includes a fluorometer, a support comprising two or more fluorescent standards, and a drive mechanism. The fluorometer comprises two or more channels, each channel includes a separate light source, an optical focus and filter assembly, and an optical signal detector, and each channel is configured to focus the light source at a detection zone. Each fluorescent reference standard of the support corresponds to a single channel of the fluorometer, and the support is arranged to accommodate two or more removable reaction vessels. The drive mechanism is configured to adjust the relative horizontal positioning between the reference standards and the fluorometer such that each of the two or more fluorescent reference standards can be positioned in or out of optical communication with its corresponding channel of the fluorometer.

Aspects of the invention are further embodied in a method of monitoring fluorometer performance in a dynamic system comprised of (a) a fluorometer comprising two or more channels, each channel having a separate light source, optical focus and filter assembly, and optical signal detector, and wherein each channel is configured to focus the light source at a detection zone, (b) a support comprising two or more fluorescent reference standards, each fluorescent reference standard corresponding to a single channel of the fluorometer, wherein the support is arranged to accommodate two or more removable receptacle vessels, and (c) a drive mechanism configured to adjust the relative horizontal positioning between the reference standards and the fluorometer such that each of the two or more fluorescent reference standards can be positioned in or out of optical communication with its corresponding channel of the fluorometer. The method comprises the steps of moving the support with respect to the fluorometer with the drive mechanism to position each of the two or more fluorescent reference standards into optical communication with the corresponding channel of the fluorometer; and using the fluorescent reference standard for monitoring the performance of the fluorometer.

According to further aspects of embodiments of the invention, the fluorescent reference standard is positioned in optical communication with the corresponding channel of the fluorometer and out of focus relative to the detection zone.

According to further aspects of embodiments of the invention, the two or more fluorescent reference standards are positioned in a linear arrangement on the support.

According to further aspects of embodiments of the invention, the support comprises two or more linear arrangements of two or more fluorescent reference standards. Each linear arrangement may comprise a set of fluorescent reference standards having emission characteristics that differ from each of the other linear arrangements of fluorescent reference standards. Furthermore, one or more of the fluorescent reference standards in the linear arrangement may have emission characteristics that differ from one or more other fluorescent reference standards in the linear arrangement, and adjacent fluorescent reference standards in the linear arrangement may have different emission characteristics. The support may comprise three linear arrangements of fluorescent reference standards, and at least one of the linear arrangements may comprise a set of fluorescent reference standards having emission characteristics that differ from the two other linear arrangements of fluorescent reference standards.

According to further aspects of embodiments of the invention, each of the fluorescent reference standard is comprised of fluorescent plastic, and the fluorescent reference standard may be pink, green, blue, or amber plastic.

According to further aspects of embodiments of the invention, only one of the two or more fluorescent reference standards can be positioned in optical communication with one of the two or more channels of the fluorometer at a time.

According to further aspects of embodiments of the invention, the fluorescent reference standard may be positioned between about 1% to 99% closer to its corresponding channel relative to the detection zone, between about 20% to 80% closer to its corresponding channel relative to the detection zone, or between about 60% to 90% closer to its corresponding channel relative to the detection zone.

According to further aspects of embodiments of the invention, the fluorescent reference standard may be positioned between about 1% to 99% further from its corresponding channel relative to the detection zone, between about 20% to 80% further from its corresponding channel relative to the detection zone, or between about 60% to 90% further from its corresponding channel relative to the detection zone. In another embodiment, the fluorescent reference standard is positioned at the same distance from its corresponding channel as the distance between the channel and the detection zone.

According to further aspects of embodiments of the invention the fluorometer is stationary, and the drive mechanism is configured to adjust the relative horizontal positioning between the reference standards and the fluorometer by adjusting the horizontal positioning of the support.

According to further aspects of embodiments of the invention, the support comprises a rotatable carousel, the fluorometer is fixed with respect to the carousel, and the drive mechanism is configured to adjust the relative horizontal positioning between the reference standards and the fluorometer by effecting angular movement of the carousel around a central axis. The drive mechanism may comprise a motor and a drive belt configured to transfer rotational motion from a drive shaft of the motor to the carousel. The fluorescent reference standards maybe positioned on an outer surface of the carousel and may be embedded in an outer surface of the carousel. According to further aspects, the carousel comprises a circular disk having a center corresponding to the central axis and a plurality of spokes extending outwardly relative to the central axis, and the fluorescent reference standards are located on one or more of the spokes. The spokes may be in a non-radial orientation with respect to the central axis.

Further aspects of the invention include two or more fluorometers. Each fluorometer comprises two or more channels, each channel includes a separate light source, an optical focus and filter assembly, and an optical signal detector, and each channel is configured to focus the light source at a detection zone. Each fluorometer may have a different light source, optical focus and filter assembly, and optical signal detector such that each fluorometer emits a different excitation signal and detects a different emission signal.

According to further aspects of embodiments of the invention, each channel of the fluorometer has a different light source, optical focus and filter assembly, and optical signal detector such that each fluorometer emits a different excitation signal and detects a different emission signal.

According to further aspects of embodiments of the invention, the channels of the fluorometer are arranged in an alternating manner such that adjacent channels emits different excitation signals and detect different emission signals.

According to further aspects of the invention, using the fluorescent standard for monitoring the performance of the fluorometer comprises measuring the intensity of the fluorescent emission of the fluorescent reference standard and comparing the measured intensity to a predetermined baseline fluorescent intensity of the fluorescent reference standard for that fluorometer.

According to further aspects of embodiments of the invention, only one fluorescent reference standard is in optical communication with its corresponding channel at a time.

According to further aspects of embodiments of the invention, the system further comprises two or more receptacle vessels containing reaction materials, and the method further comprises monitoring the progress of a reaction occurring in each receptacle vessel with the fluorometer.

According to further aspects of embodiments of the invention, monitoring the performance of the fluorometer occurs in sequence with monitoring the progress of the reaction occurring in each of the two or more receptacle vessels.

Further aspects of the invention are embodied in a system for monitoring reactions within a plurality of receptacle vessels. The system includes an incubator having a temperature-controlled chamber, a movable receptacle carrier disposed within the temperature-controlled chamber, one or more fixed fluorometers, one or more fluorescent reference standards, and a controller. The receptacle carrier is configured to carry a plurality of receptacle vessels and to move the receptacle vessels within the temperature-controlled chamber. Each fluorometer is configured to measure a fluorescent emission and is positioned with respect to the receptacle carrier to measure fluorescent emissions from receptacle vessels carried on the receptacle carrier into an operative position with respect to each fluorometer. The fluorescent reference standards are mounted on the receptacle carrier. The controller is configured to control operation of the receptacle carrier and the one or more fluorometers. The controller is configured to move the receptacle carrier with respect to the one or more fluorometers to place a receptacle vessel into an operative position with respect to each fluorometer. The controller then activates each fluorometer to measure the fluorescent emission intensity from the sample contained in the receptacle vessel that is in the operative position with respect to the fluorometer and determines a characteristic of the reaction based on the measured fluorescent emission intensity from the sample contained in the receptacle vessel. The controller then moves the receptacle carrier with respect to the one or more fluorometers to place a fluorescent standard into optical communication with at least one fluorometer and activates the fluorometer to measure the fluorescent emission intensity of the fluorescent standard that is in optical communication with the fluorometer. The controller then determines a deviation of the measured fluorescent emission intensity of the fluorescent standard from an expected fluorescent emission intensity. If the deviation exceeds a threshold, the controller generates an error signal, and if the deviation does not exceed a threshold, the controller continues operation of the instrument.

Furthermore in an instrument configured to determine a characteristic of a sample from the intensity of a fluorescent emission from the sample, wherein the sample is contained in a receptacle vessel that is carried on a movable receptacle carrier, and the intensity of the fluorescent emission is measured by a fluorometer that is fixed with respect to the receptacle carrier and is constructed and arranged to measure the intensity of fluorescent emission from a sample contained in a receptacle vessel that is moved by the receptacle carrier into a detection zone with respect to the fluorometer, further aspects of the invention are embodied in an automated method for detecting failure or deteriorated performance of the fluorometer with a fluorescent reference standard mounted on the receptacle carrier. The receptacle carrier is moved with respect to the fluorometer to periodically place the receptacle vessel into the detection zone of the fluorometer, and a plurality of measurements of the intensity of the fluorescent emission from the sample contained in the receptacle vessel are taken with the fluorometer. After taking a plurality of measurements, the receptacle carrier is moved with respect to the fluorometer to place the fluorescent reference standard into optical communication with the fluorometer, and a test measurement of the emission intensity of the fluorescent reference standard is taken with the fluorometer. A deviation of the test measurement from a predetermined baseline emission intensity of the fluorescent reference standard is determined. If the deviation determined exceeds a threshold, an error signal is generated. If the deviation does not exceed the threshold, operation of the instrument is continued by repeating the steps of taking a plurality of measurements from a sample, taking a test measurement of the fluorescent reference standard, and determining whether a deviation between the test measurement and the baseline exceeds the threshold until a stop condition is reached.

According to a further aspect of the invention, determining the baseline emission intensity comprises the steps of moving the receptacle carrier with respect to the fluorometer to place the fluorescent reference standard into optical communication with the fluorometer before taking a plurality of measurements of fluorescent emission from samples, taking an initial measurement of the fluorescent emission intensity of the fluorescent reference standard with the fluorometer, and storing the initial measurement as the predetermined baseline emission intensity.

These and other features, aspects, and advantages of the present invention will become apparent to those skilled in the art after considering the following detailed description, appended claims and accompanying drawings.

DETAILED DESCRIPTION OF THE PREFERRED EMBODIMENT

Multiple Receptacle Devices

Figure 1:
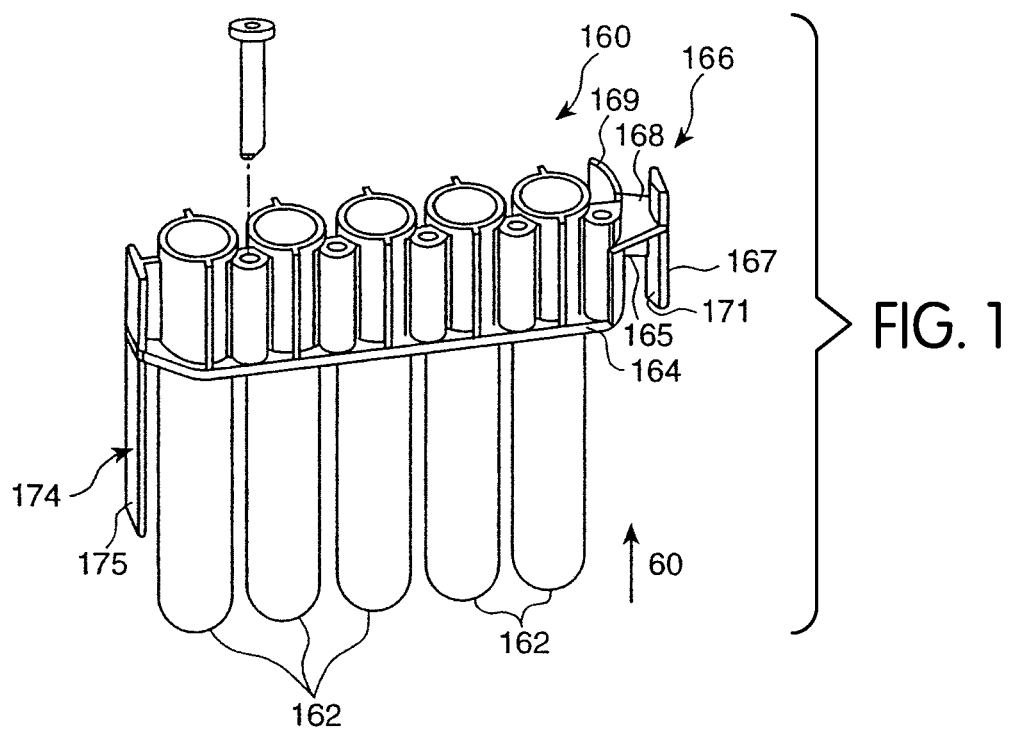
FIG. 1 is a perspective view of a reaction receptacle in the form of a multiple receptacle device unit employed in combination with an apparatus embodying aspects of the present invention.

Referring to FIG. 1, a reaction receptacle in the form of a multiple receptacle device ("MRD") 160 comprises a plurality of individual receptacle vessels, or reaction tubes, 162, preferably five. The receptacle vessels 162, preferably in the form of cylindrical tubes with open top ends and closed bottom ends, are connected to one another by a connecting rib structure 164 which defines a downwardly facing shoulder extending longitudinally along either side of the MRD 160.

The MRD 160 is preferably formed from injection molded polypropylene, such as those sold by Montell Polyolefins, of Wilmington, Del., product number PD701NW or Huntsman, product number P5M6K-048. In an alternative embodiment, the receptacle vessels 162 of the MRD are releasably fixed with respect to each other by means such as, for example, a sample tube rack.

An arcuate shield structure 169 is provided at one end of the MRD 160. An MRD manipulating structure 166 extends from the shield structure 169. The manipulating structure is adapted to be engaged by a transport mechanism for moving the MRD 160 between different components of a diagnostic analyzer. An exemplary transport mechanism that is compatible with the MRD 160 is described in U.S. Pat. No. 6,335,166. The MRD manipulating structure 166 comprises a laterally extending plate 168 extending from shield structure 169 with a vertically extending piece 167 on the opposite end of the plate 168. A gusset wall 165 extends downwardly from lateral plate 168 between shield structure 169 and vertical piece 167. Vertical piece 167 comprises a convex face 171 facing the shield structure 169.

Figure 2:
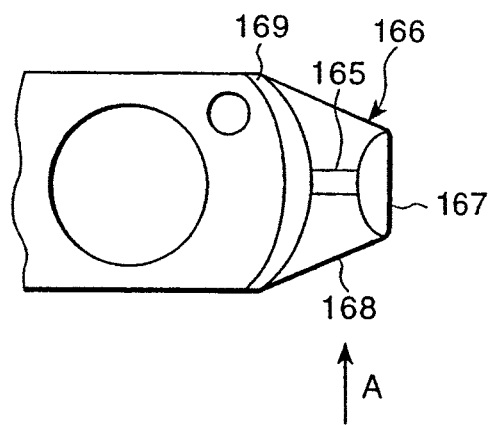
FIG. 2 is an enlarged bottom view of a portion of the multiple receptacle device, viewed in the direction of arrow "60" in FIG. 1.

As shown in FIG. 2, the shield structure 169 and vertical piece 167 have mutually facing convex surfaces. The MRD 160 may be engaged by a transport mechanism and other components, by moving an engaging member laterally (in the direction "A") into the space between the shield structure 169 and the vertical piece 167. The convex surfaces of the shield structure 169 and vertical piece 167 provide for wider points of entry for an engaging member undergoing a lateral relative motion into the space.

A label-receiving structure 174 having a flat label-receiving surface 175 is provided on an end of the MRD 160 opposite the shield structure 169 and MRD manipulating structure 166. Human and/or machine-readable labels, such as scannable bar codes, can be placed on the surface 175 to provide identifying and instructional information on the MRD 160.

Further details regarding the MRD 160 may be found in U.S. Pat. No. 6,086,827.

Nucleic Acid Diagnostic Assays

Aspects of the present invention involve apparatus and procedures that can be used in conjunction with nucleic acid diagnostic assays, including "real-time" amplification assays and "end-point" amplification assays.

Real-time amplification assays can be used to determine the presence and amount of a target nucleic acid in a sample which, by way of example, is derived from a pathogenic organism or virus. By determining the quantity of a target nucleic acid in a sample, a practitioner can approximate the amount or load of the organism or virus in the sample. In one application, a real-time amplification assay may be used to screen blood or blood products intended for transfusion for bloodborne pathogens, such as hepatitis C virus (HCV) and human immunodeficiency virus (HIV). In another application, a real-time assay may be used to monitor the efficacy of a therapeutic regimen in a patient infected with a pathogenic organism or virus, or that is afflicted with a disease characterized by aberrant or mutant gene expression. Real-time amplification assays may also be used for diagnostic purposes, as well as in gene expression determinations.

In addition to implementation of the invention in conjunction with real-time amplification assays, the invention may also be implemented in conjunction with end point amplification assays. In end-point amplification assays, the presence of amplification products containing the target sequence or its complement is determined at the conclusion of an amplification procedure. The determination may occur in a detection station that may be located externally to the incubator in which the amplification reactions occur. In contrast, in "real-time" amplification assays, the amount of amplification products containing the target sequence or its complement is determined during an amplification procedure. In the real-time amplification assay, the concentration of a target nucleic acid can be determined using data acquired by making periodic measurements of signals that are functions of the amount of amplification product in the sample containing the target sequence, or its complement, and calculating the rate at which the target sequence is being amplified from the acquired data.

In an exemplary real-time amplification assay, the interacting labels include a fluorescent moiety, or other emission moiety, and a quencher moiety, such as, for example, 4-(4-dimethylaminophenylazo) benzoic acid (DABCYL). The fluorescent moiety emits light energy (i.e., fluoresces) at a specific emission wavelength when excited by light energy at an appropriate excitation wavelength. When the fluorescent moiety and the quencher moiety are held in close proximity, light energy emitted by the fluorescent moiety is absorbed by the quencher moiety. But when a probe hybridizes to nucleic acid present in the sample, the fluorescent and quencher moieties are separated from each other and light energy emitted by the fluorescent moiety can be detected. Fluorescent moieties which are excited and emit at different and distinguishable wavelengths can be combined with different probes. The different probes can be added to a sample, and the presence and amount of target nucleic acids associated with each probe can be determined by alternately exposing the sample to light energy at different excitation wavelengths and measuring the light emission from the sample at the different wavelengths corresponding to the different fluorescent moieties.

Where an amplification procedure is used to increase the amount of target sequence, or its complement, present in a sample before detection can occur, it is desirable to include a "control" to ensure that amplification has taken place and, thereby, to avoid false negatives. Such a control can be a known nucleic acid sequence that is unrelated to the sequence(s) of interest. A probe (i.e., a control probe) having specificity for the control sequence and having a unique fluorescent dye (i.e., the control dye) and quencher combination is added to the sample, along with one or more amplification reagents needed to amplify the control sequence, as well as the target sequence(s). After exposing the sample to appropriate amplification conditions, the sample is alternately exposed to light energy at different excitation wavelengths (including the excitation wavelength for the control dye) and emission light is detected. Detection of emission light of a wavelength corresponding to the control dye confirms that the amplification was successful (i.e., the control sequence was indeed amplified), and thus, any failure to detect emission light corresponding to the probe(s) of the target sequence(s) is not likely due to a failed amplification. Conversely, failure to detect emission light from the control dye may be indicative of a failed amplification, thus rendering any results from that assay suspect. Alternatively, failure to detect emission light may be due to failure or deteriorated mechanical and/or electrical performance of an instrument (described below) for detecting the emission light. The present invention concerns methods and apparatus for detecting such failure or deteriorated performance. In the present context, "performance" means the reliability of the operation of the instrument such that output of the instrument may be relied upon in deriving an assay or test result. Instrument failure or deteriorated performance may be detected, in accordance with principles of the invention, by objectively measurable characteristics of the output of the instrument that deviate from an output that would be normally expected under similar operation conditions if the instrument were operating properly. Examples of such objectively measurable characteristics that may be indicative of instrument failure or deteriorated performance may include an unexpected decrease in the intensity of the instrument output or a spike in the instrument output.

Systems and methods for performing real-time amplification assays are described in Macioszek et al., "Methods for Performing Multi-Formatted assays," U.S. Pat. No. 7,897,337. Systems and methods for end-point detection are described in Ammann, et al., "Automated Process For Isolating and Amplifying a Target Nucleic Acid Sequence" U.S. Pat. No. 6,335,166.

In accordance with aspects of the present invention, amplification assays are performed in an incubator, such as incubator 200, features of which are shown in FIGS. 3-10. Incubator 200 is a rotary incubator in the sense that MRDs 160 are carried on a rotary carrier structure (e.g., a carousel) within a controlled temperature housing. Incubator 200 includes signal detectors, or signal detector blocks, 400 attached thereto for detecting, in a real-time manner, the amplification occurring within the reaction tubes 162 of an MRD 160 carried in the incubator, for example, by measuring the fluorescence emitted by a dye or dyes within each reaction tube 162 of the MRD 160 when the MRD 160 is illuminated with an excitation light corresponding to each dye. The incubator 200 can be integrated into an automated diagnostic analyzer (not shown) that may include one or more receptacle transport mechanisms for placing MRDs 160 into the incubator 200 and removing MRDs 160 from the incubator 200.

Figure 3:
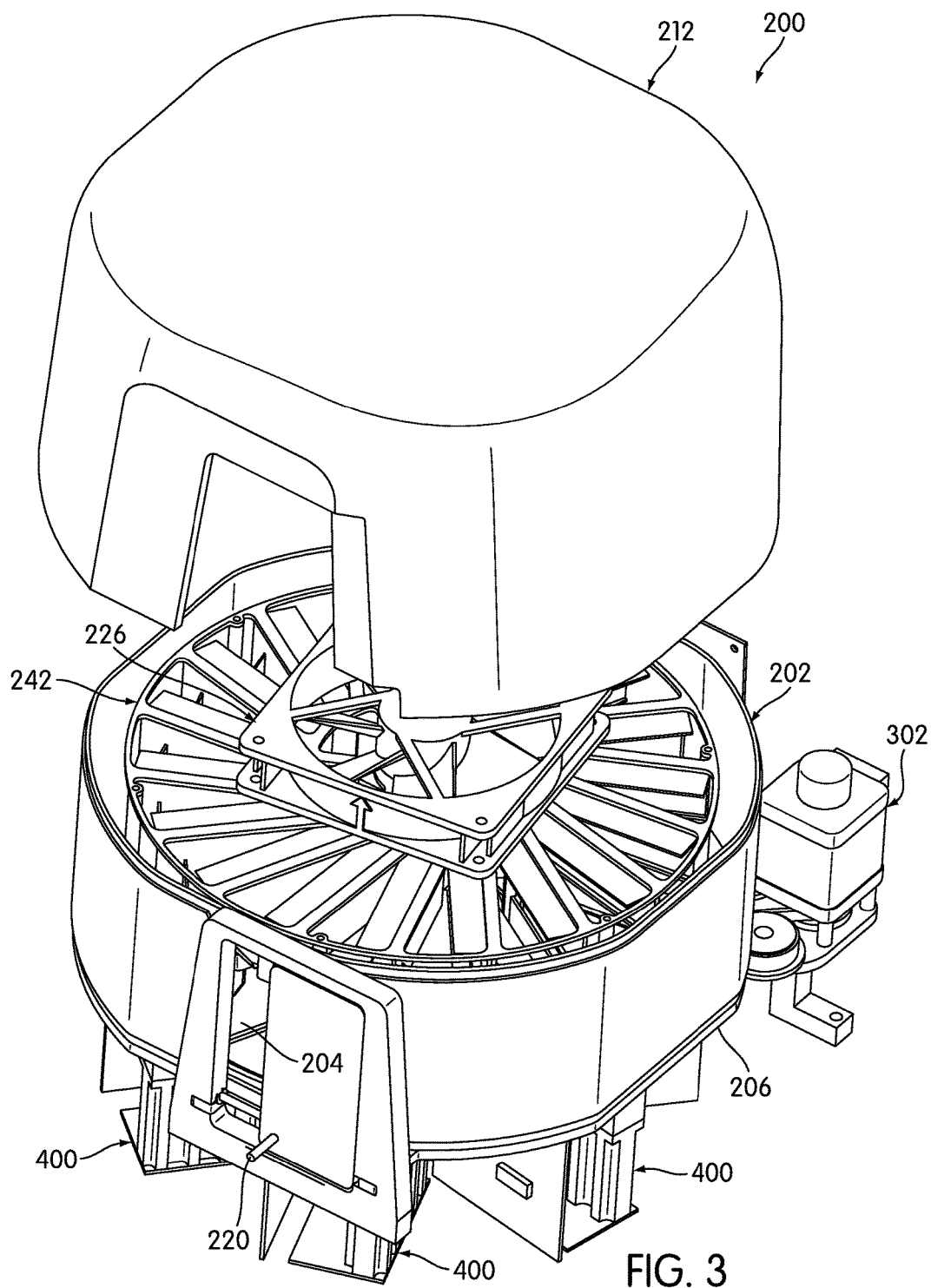
FIG. 3 is an exploded perspective view of an incubator configured to hold a plurality of receptacles while subjecting the reaction receptacles to prescribed temperature conditions and including signal detectors for detecting signals emitted by the contents of the reaction receptacles during an incubation process.

Features of an incubator 200, adapted for use in conjunction with the present invention, are shown in FIGS. 3-10. FIG. 3 shows an exploded perspective view of the incubator 200. The incubator 200 includes a housing that comprises an outer wall 202, a bottom wall 206, and a top wall (not shown), all of which are covered by a thermal insulating shroud, or hood, 212, which is shown lifted off the remainder of the incubator. The side, bottom and top walls are preferably formed of aluminum, and the insulating hood is preferably made from a suitable insulating material, such as polyurethane foam. A receptacle carrier 242, preferably in the form of a carousel rotatably mounted within the housing, is configured for carrying a plurality of reaction receptacles. Receptacles, such as MRDs 160, can be inserted into the receptacle carrier 242 and removed from the receptacle carrier 242 through a receptacle opening 204 formed in the sidewall 202. Receptacle opening 204 is covered by the sliding door 216 of a door assembly 214 (described in more detail below).

One or more signal detectors 400 are disposed beneath the bottom wall 206 of the incubator housing and are configured for detecting signals emitted by the contents of MRDs 160 carried on the receptacle carrier 242 within the incubator 200. The signal detectors 400, which may comprise fluorometers for detecting fluorescent signals, are described in further detail below.

Heat may be generated within the incubator 200 by any suitable means. In one embodiment, resistive heating elements are disposed on the sidewall 202 of the incubator housing. Other suitable heating elements may include, for example, Peltier' thermoelectric heating elements. The heating elements may be under microprocessor control for maintaining a constant, desired temperature, and the incubator 200 may further include one or more temperature-sensing elements for providing temperature level signals to the microprocessor controller.

A circulating fan 226 may be positioned within the incubator housing, for example, atop the receptacle carrier 242. In one embodiment, fan 226 is an axial fan, as shown, configured for generating airflow through the receptacle carrier 242 and within the incubator 200.

Figure 4:
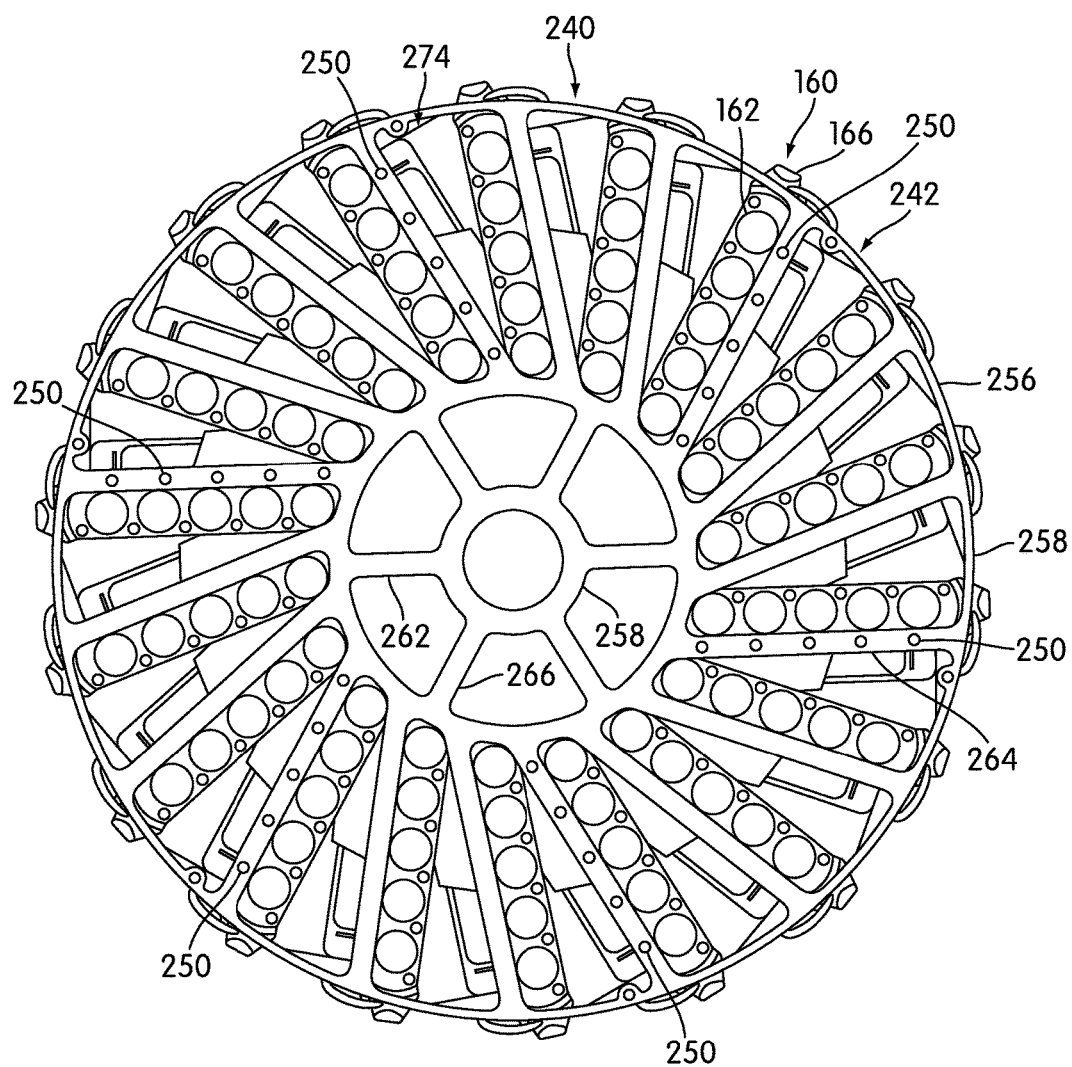
FIG. 4 is a bottom plan view of a receptacle carrier carousel of the incubator.
Figure 5:
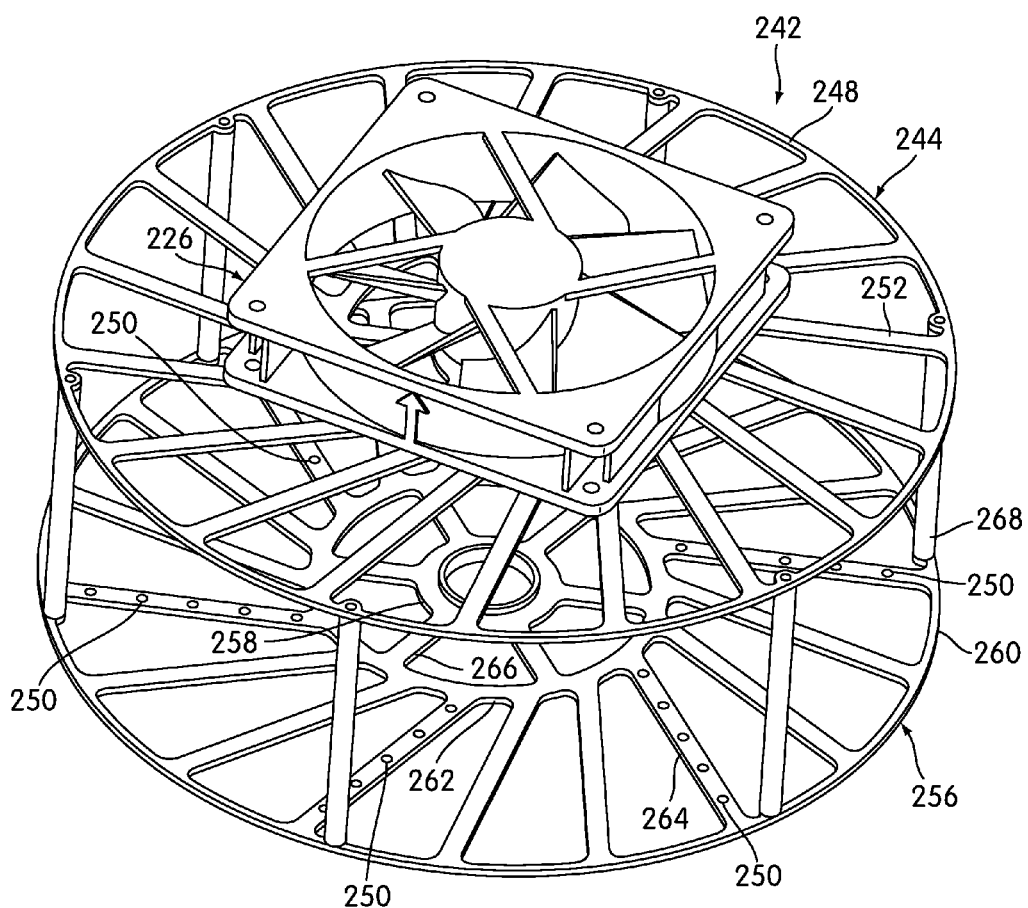
FIG. 5 is a perspective view of assembled components of a receptacle carrier carousel of the incubator and a circulating fan for generating airflow within the incubator.

Further details concerning the construction of the receptacle carrier 242 are shown in FIGS. 4 and 5. FIG. 4 is a bottom plan view of the receptacle carrier 242 with a plurality of MRDs 160 carried thereon. FIG. 5 is a perspective view of a portion of the receptacle carrier 242 and showing the fan 226 mounted atop the carrier 242.

Carrier 242 comprises an upper disk 244 and an identical lower disk 256. As shown in FIGS. 4 and 5, the lower disk includes an inner ring 258, an outer ring 260, and an intermediate ring 262 disposed concentrically between the inner ring 258 and outer ring 260. Inner radial spokes 266 extend between the inner ring 248 and the intermediate ring 262. Outer spokes 264 extend between the intermediate ring 262 and the outer ring 260 and are, in this embodiment, in a non-radial orientation, meaning that each spoke is configured obliquely with respect to a true-radial orientation relative to the center of the intermediate ring 262 and outer ring 260. Optical reference standards 250 are provided on selected outer spokes 264 of the lower disk 256 of the receptacle carrier 242. The purpose of these optical reference standards 250 will be described below.

The upper disk 244 has a similar construction, but only outer ring 248 and outer spokes 252 are visible in FIG. 5. The upper disk 244 further includes an inner ring, an intermediate ring, and inner spokes, all of which are obstructed from view by the fan 226 in FIG. 5.

The upper disk 244 and the lower disk 256 are secured relative to one another in a parallel, spaced-apart orientation by a plurality of spacer posts 268 disposed at angular intervals around the perimeters of the upper disk 244 and lower disk 256. Each spacer post 268 may be secured in place by means of a suitable fastener, such as a screw, extending through a hole in the upper disk 244 or lower disk 256 and into an opening (e.g. a threaded opening) formed in each end of each of the spacer posts 268.

The receptacle carrier 242 further includes a plurality of receptacle dividers 274 extending between each of the outer spokes 264 of the lower disk 256 and corresponding outer spokes 252 of the upper disk 244. The spaces between adjacently disposed receptacle dividers 274 define receptacle stations 240, each configured to receive a single MRD 160. As shown in FIG. 4, which is a bottom plan view of a receptacle carrier carousel of the incubator, each MRD 160 is carried in a generally vertical orientation with the lower ends of each receptacle vessel 162 exposed at the bottom of the receptacle carrier 242 and with the receptacle manipulating structure 166 of each MRD 160 extending radially beyond the outer perimeter of the receptacle carrier 242.

Figure 6:
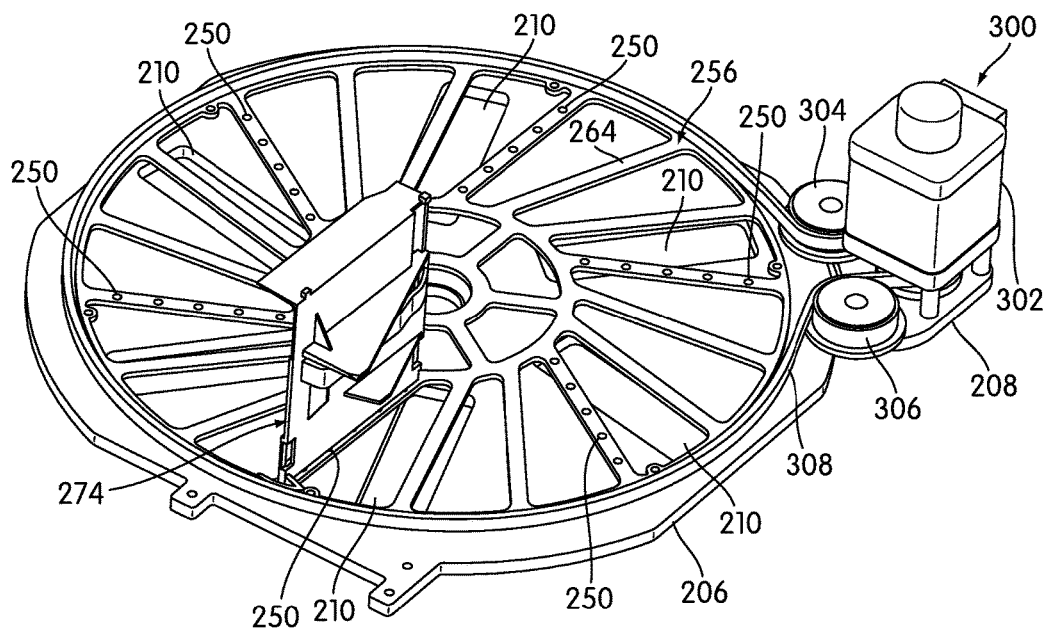
FIG. 6 is a perspective view of a bottom wall of the incubator housing, a portion of the receptacle carrier, and a receptacle carrier drive assembly.
Figure 7:
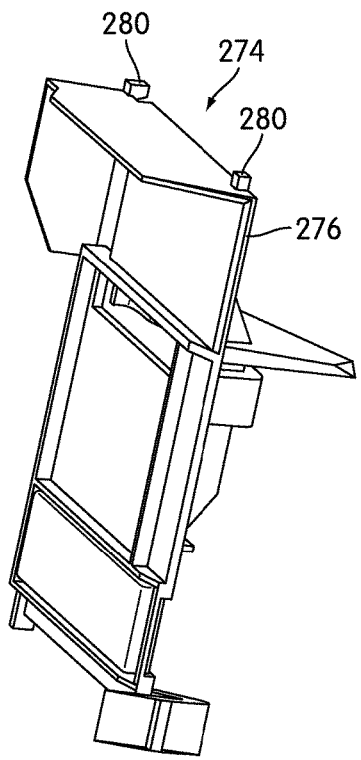
FIG. 7 is a perspective view of a receptacle divider of the receptacle carrier.
Figure 8:
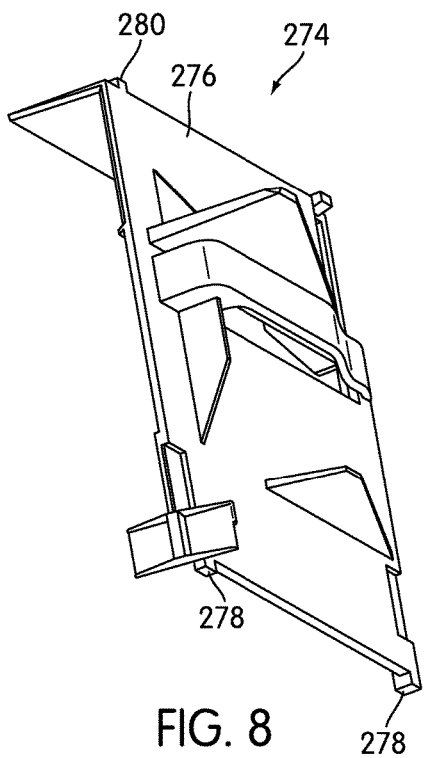
FIG. 8 is a perspective view of the receptacle divider from an opposite side of the divider.

Details of the receptacle dividers are shown in FIGS. 6-8. As noted, each receptacle divider 274 is attached to one of the outer spokes 264 of the lower disk 256, as shown in FIG. 6. The receptacle divider 274 includes a divider wall 276 that is oriented generally vertically when the divider 274 is installed between the upper disk 244 and lower disk 256. The divider wall 276 includes lower positioning posts 278 configured to be inserted into mating openings formed in the lower disk 256 (not shown) and upper positioning posts 280 configured to be inserted into mating openings (not shown) formed in the upper disk 244. In an embodiment of the invention, the incubator 200 holds eighteen MRDs 160 at a time, each spaced at 20° increments around the carousel.

A drive assembly 300 of the receptacle carrier 242 includes a motor 302 mounted on a motor mount portion 208 of the bottom wall 206 of the incubator housing, guide wheels 304 and 306, and a drive belt 308. Drive belt 308 is secured around a drive shaft (not shown) of the motor 302, around the guide wheels 304 and 306, and further over the belt drive supports 298 of the plurality of dividers 274 mounted between the upper disk 244 and lower disk 256. As noted, each drive belt support 298 may include a vertical rib 299 for engaging teeth (not shown) of the drive belt 308. As shown in FIG. 6, which shows a perspective view of a bottom wall of the incubator housing, a portion of the receptacle carrier, and a receptacle carrier drive assembly, the bottom wall 206 of the incubator housing includes a plurality of elongated openings 210, preferably formed at equal angular intervals about a point corresponding to the axis of rotation of the receptacle carrier 242. The openings 210 are oriented at the same angle at which each MRD 160 will be oriented when carried on the receptacle carrier 242, and each opening 210 is configured to receive an upper end of a signal detector 400 extending into the incubator 200 for detecting signals emitted by the contents of the MRDs 160 during the incubation process. Motor 302 is preferably a stepper motor under microprocessor control to enable precise control of rotation of the receptacle carrier 242. A "home" position sensor (not shown) indicates when the receptacle carrier 242 is in a specified rotational position, and the motor 302 is provided with an encoder. Accordingly, movement of the receptacle carrier 242 can be controlled, e.g., by a microprocessor receiving signals from the home sensor and an encoder coupled to motor 302 to control and monitor the angular movement and positioning of the carrier 242, to sequentially place each MRD 160 on the receptacle carrier 242 into a signal detection position above the openings 210.

Figure 9:
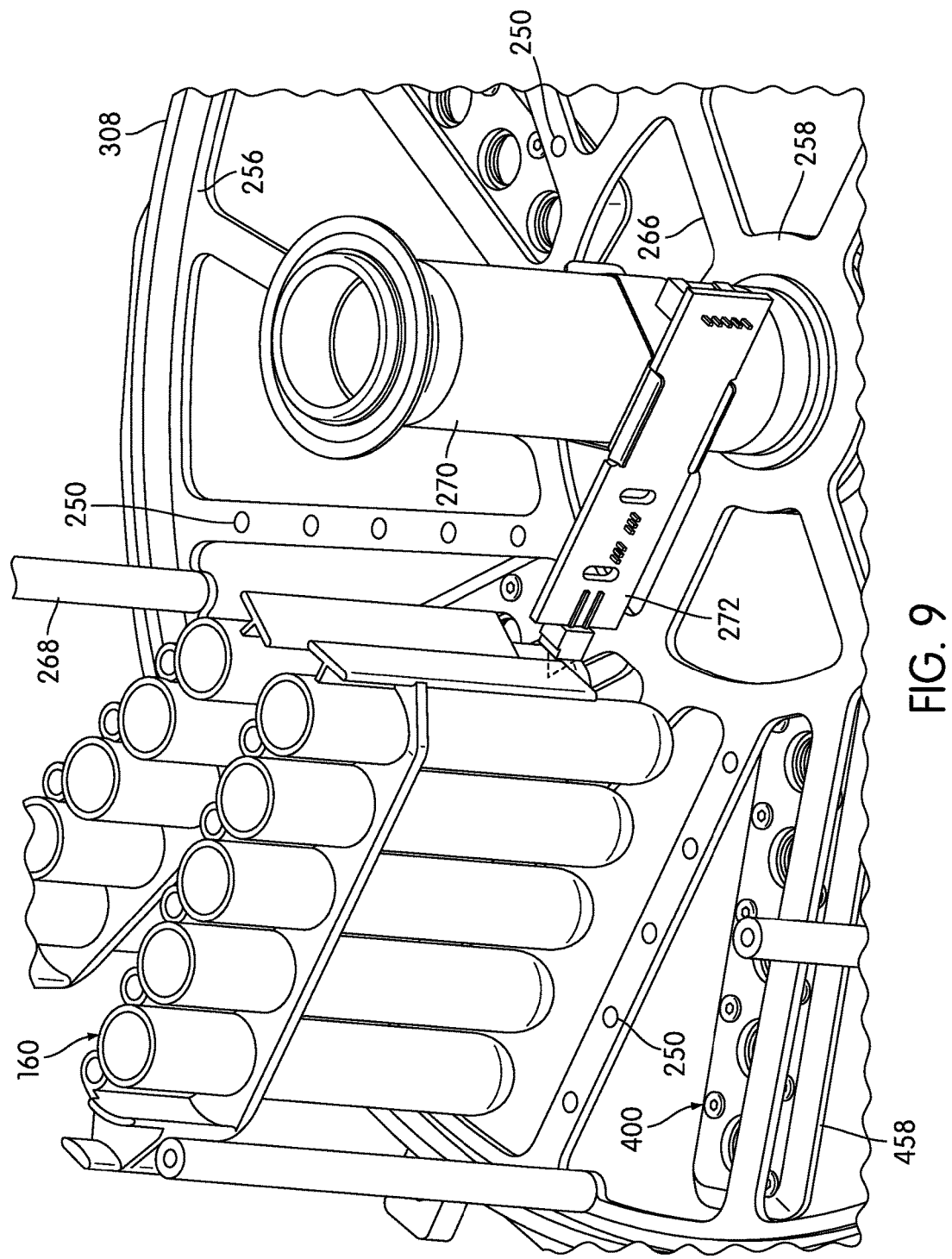
FIG. 9 is a partial perspective view of components of the receptacle carrier of the incubator including a receptacle presence sensor for detecting the presence of reaction receptacles on the receptacle carrier.

As shown in FIG. 9, which shows a partial perspective view of components of the receptacle carrier of the incubator, the receptacle carrier 242 further includes a center post 270 extending between the inner ring 258 of the lower disk 256 and the inner ring of the upper disk 244 (not shown in FIG. 9). A receptacle presence sensor 272 is mounted to the center post 270 and is configured to detect the presence of an MRD 160 inserted into a receptacle station 240 of the receptacle carrier 242. Microprocessor control, which controls and monitors the angular position of the receptacle carrier 242, also monitors the location of each specific MRD 160, which may be identified by, e.g., a label, such as a machine-readable bar-code or an RFID tag. That is, when an MRD 160, identified via its label or other means, is moved into the incubator 200, the angular position of the receptacle station 240 into which that MRD 160 is inserted is determined and tracked to monitor the position of that MRD 160 at all times while the MRD is inside the incubator 200.

With reference to FIGS. 9 and 10-14, the signal detectors 400 are part of a system that measures, for example, the concentration of unquenched fluorescent dye molecules within the contents of receptacle vessels 162 of MRDs 160 carried on the receptacle carrier 242. The assay performed within each receptacle vessel 162 of each MRD 160 may be designed such that the fluorescent signal increases as the concentration of target is increased by amplification. The signal detector 400 (e.g., a fluorometer) is used to monitor the amplification process by monitoring the emergence of the fluorescent signal.

An exemplary embodiment of the incubator 200 may include between three and six signal detectors 400, where each detector is designed to measure a particular fluorescent dye (i.e., color). Each signal detector 400 houses, for example, five individual detectors. The five individual detectors (also referred to herein as "channels") are spaced relative to each other with the same spacing as that of the receptacle vessels 162 of each MRD 160. The signal detector 400 may be provided with additional or fewer individual detectors, but the number of detectors generally corresponds to the number of receptacle vessels 162 in each MRD 160. The signal detectors 400 are mounted to the amplification incubator 200 with such an orientation that each of them can detect signal emitted by the contents of each receptacle vessel 162 of an MRD 160 when the receptacle carrier 242 stops at preset angular increments corresponding to the angular positions of the signal detectors 400. Therefore, each MRD 160 can be scanned by each signal detector 400 once per revolution of the carrier 242.

Figure 10:
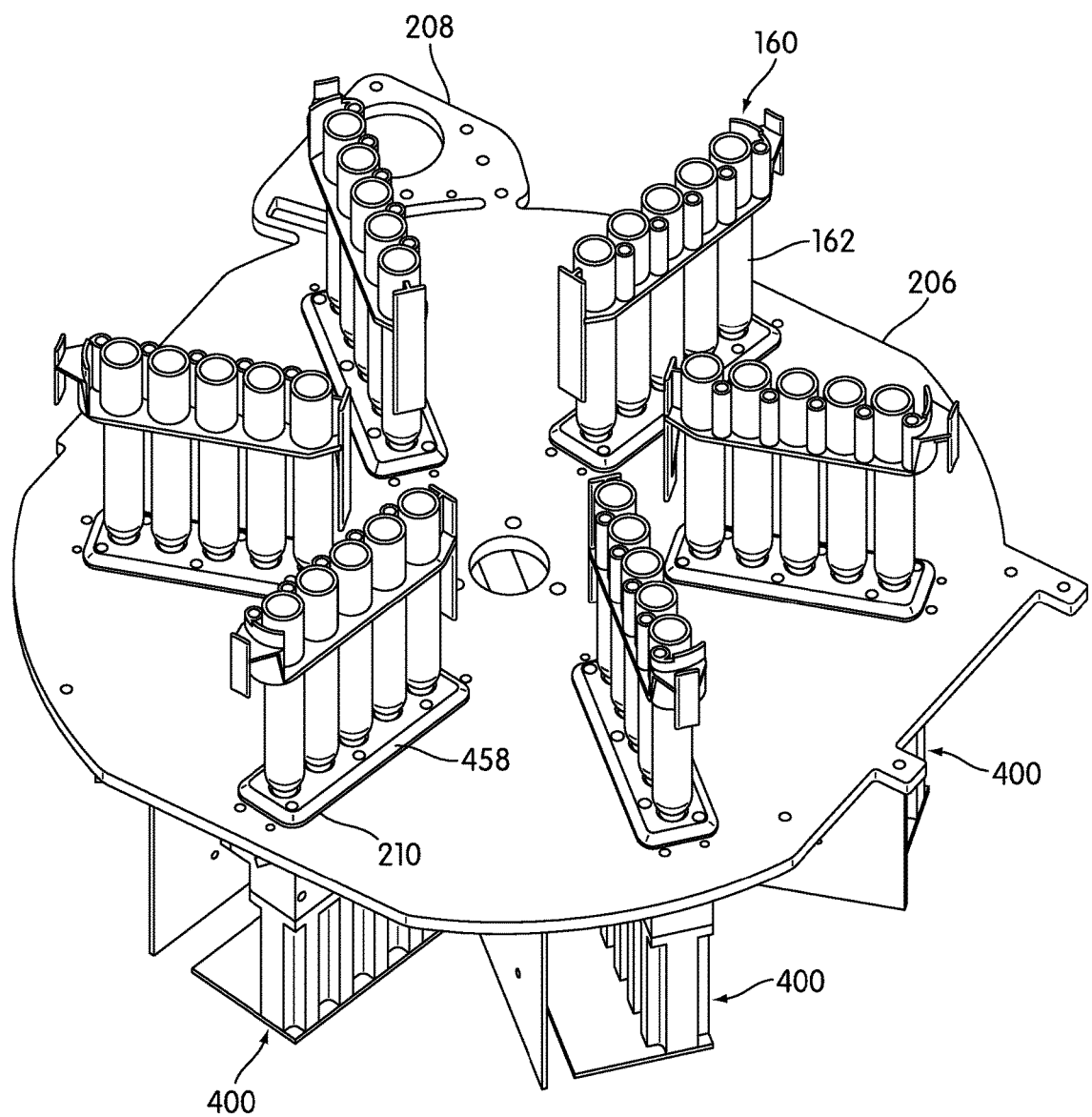
FIG. 10 is a partial perspective view of a portion of the incubator including the incubator floor, signal detectors disposed beneath the incubator floor, and reaction receptacles disposed in signal detecting positions with respect to the signal detectors.

As shown in FIG. 10, which is a partial perspective view of a portion of the incubator, in one embodiment, six signal detectors 400 are constructed and arranged to detect signals emitted by the contents of each of the five receptacle vessels 162 of six different MRDs 160 carried within the housing of the incubator 200. That is, each signal detector 400 is configured to detect a signal emitted by each of the five receptacle vessels 162 of an MRD 160 operatively positioned with respect to the signal detector 400 by the carrier 242. The signal detectors 400 may be of substantially identical constructions, but each may be adapted to detect a signal characteristic of a different measureable or detectable value. For example, each signal detector 400 may be configured to detect fluorescence of a different wavelength (i.e., color), and thus each may be configured, or tuned, to detect a different fluorescent dye within the contents of the receptacle vessel 162. Each signal detector 400 may also be configured to emit light at a predefined wavelength or within a range of wavelengths. The wavelength of the emitted light from the signal detector 400 frequently corresponds to an excitation wavelength window of a fluorescent dye within the contents of the receptacle vessel 162.

The motor 302, which drives the receptacle carrier 242, is under the control of a microprocessor which may receive signals from a home sensor coupled to the carrier 242, a timer, and an encoder coupled to the motor 302 for controlling movement and angular positioning of the carrier 242. The carrier 242 is controlled to (a) move MRD(s) 160 into operative, sensing positions with respect to the signal detector(s) 400, (b) pause for a sufficient period of time to permit the signal detector(s) to take and process a signal reading from the MRD operatively positioned with respect to it, and (c) index the carrier 242 to position the next MRD(s) 160 into operative position(s) with respect to the signal detector(s) 400.

Figure 11:
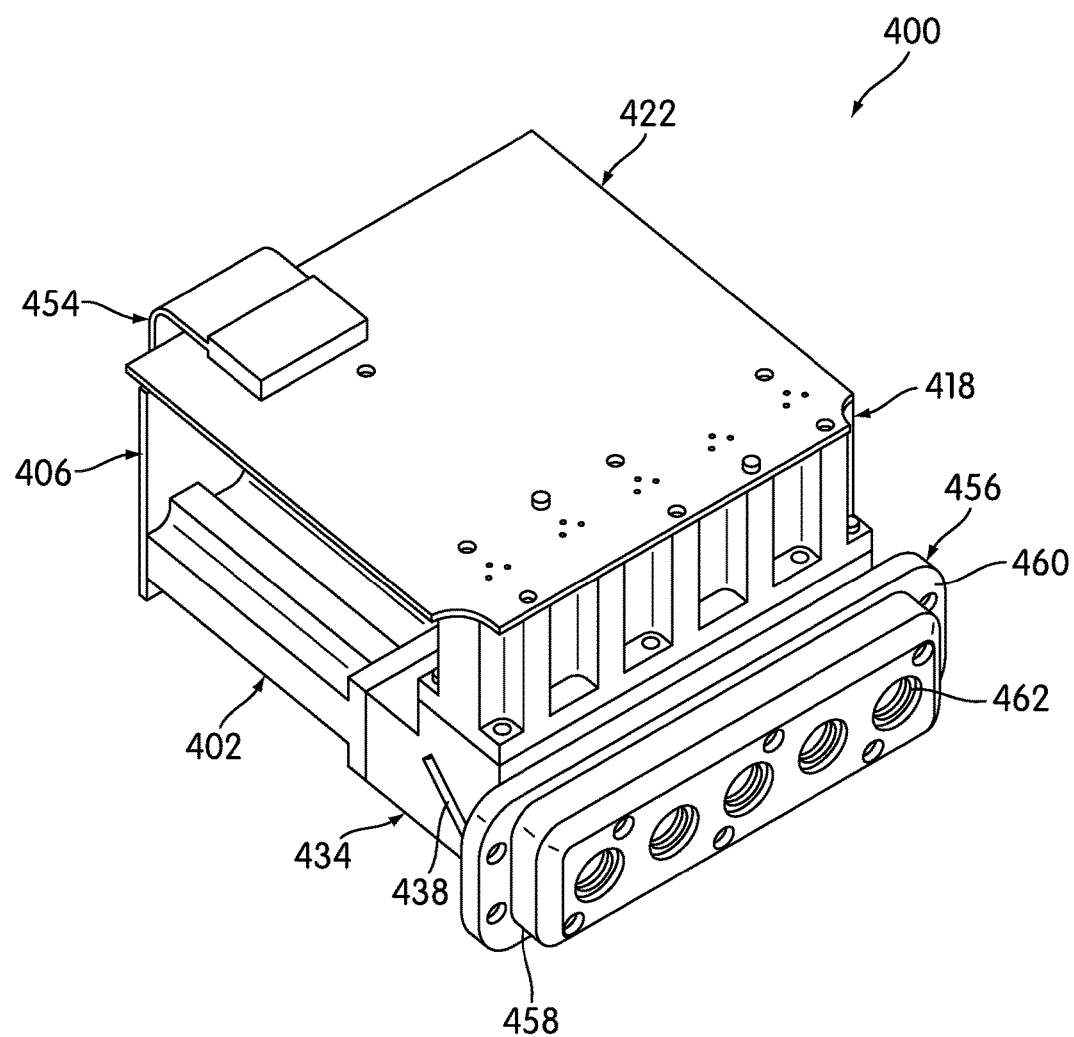
FIG. 11 is a perspective view of a signal detector for use in conjunction with the present invention.
Figure 12:
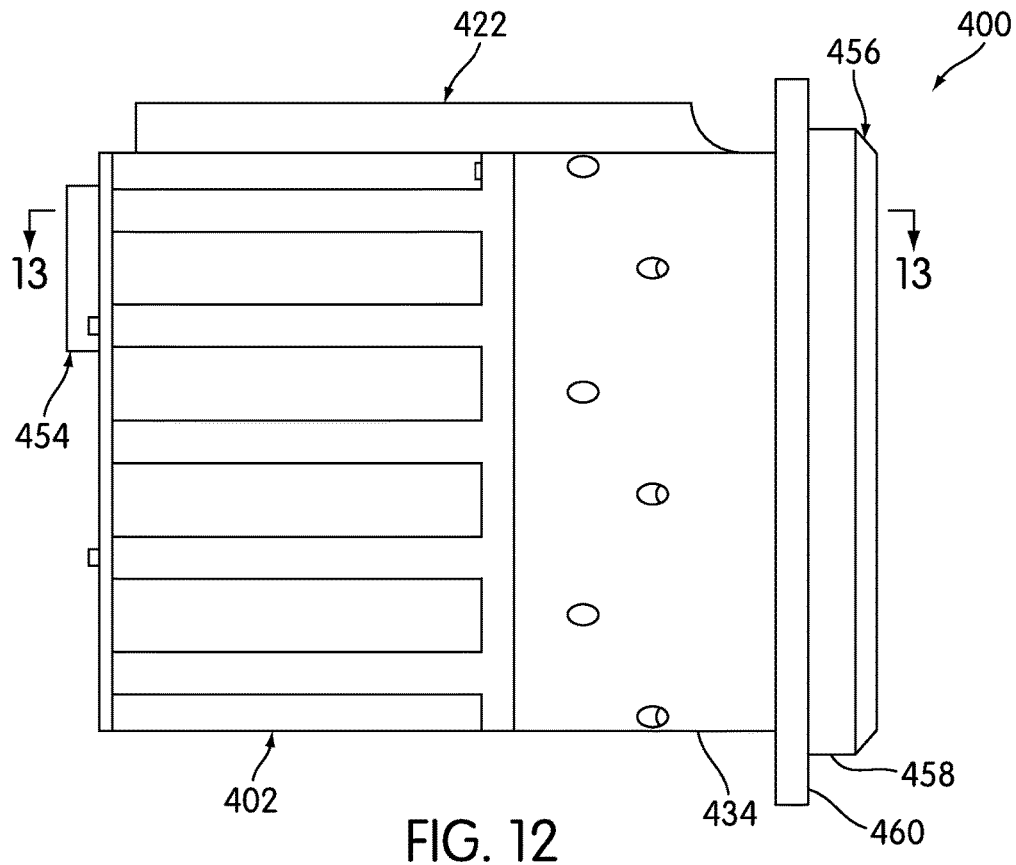
FIG. 12 is a bottom plan view of the signal detector.

Details of a signal detector 400 for use in conjunction with the present invention are shown in FIGS. 11-14. As shown in FIG. 11, which is a perspective view of a signal detector, the detector 400 includes a housing that comprises a detector housing 418 and an excitation housing 402, both connected at a right angle with respect to each other to a lens and filter, or optics, housing 434. An interface cap 456 is attached to the optics housing 438. Each of the housing components 402, 418 and 434 may be made from, for example, machined aluminum and secured to one another by suitable fasteners, such as screws, and is preferably anodized. The interface cap 456 is preferably machined from non-thermally conductive material, such as Delrin®, so as to minimize thermal conduction between the incubator 200 and the detector 400. An excitation printed circuit board ("PCB") 406 is connected to an end of the excitation housing 402, and a detector PCB 422 is connected to an end of the detector housing 418. Excitation and detector circuitry disposed on the excitation PCB 406 and the detector PCB 422, respectively, are described below. A flexible cable 454 connects the excitation PCB 406 with the detector PCB 422.

The interface cap 456 includes a rim flange 460 surrounding the periphery of the cap 456 and a dome portion 458 projecting above the rim flange 460. As shown, for example, in FIG. 10, the dome 458 of the interface cap 456 extends into the detector opening 210 formed in the bottom wall 206 of the incubator 200, and the rim flange 460 abuts the bottom portion of the bottom wall 206 surrounding the detector opening 210 so as to provide a light-tight seal between the interface cap 456 and the bottom wall 206. A gasket material may be provided between the rim flange 460 and the bottom wall 206 to further enhance the light-tight seal. Five detection openings 462 are provided in the interface cap 456.

Figure 13:
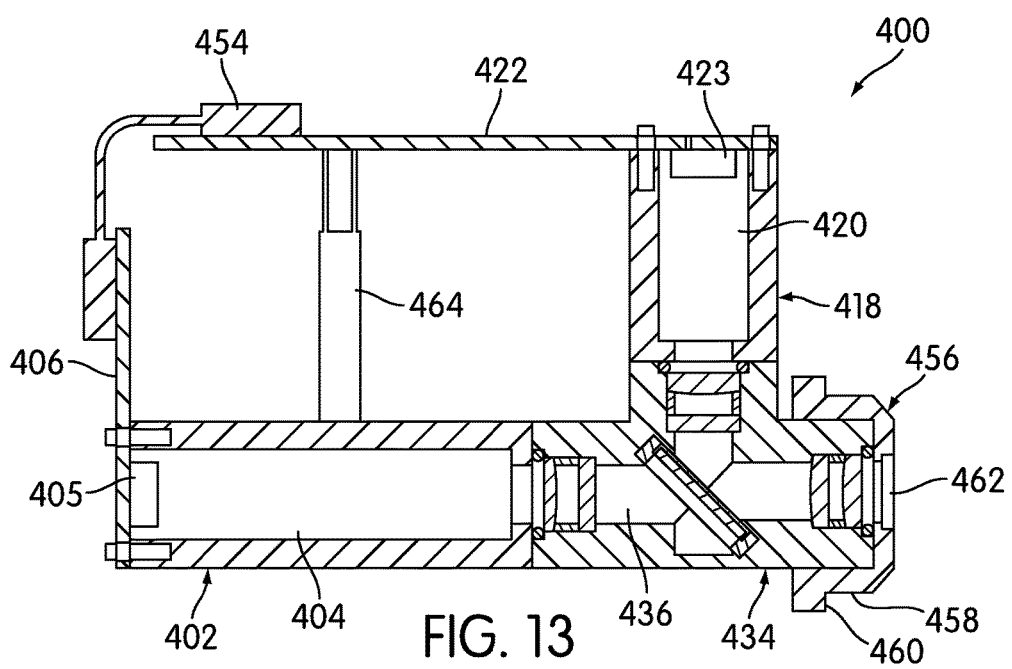
FIG. 13 is a side cross-sectional view of the signal detector taken along the line 13-13 in FIG. 12.
Figure 14:
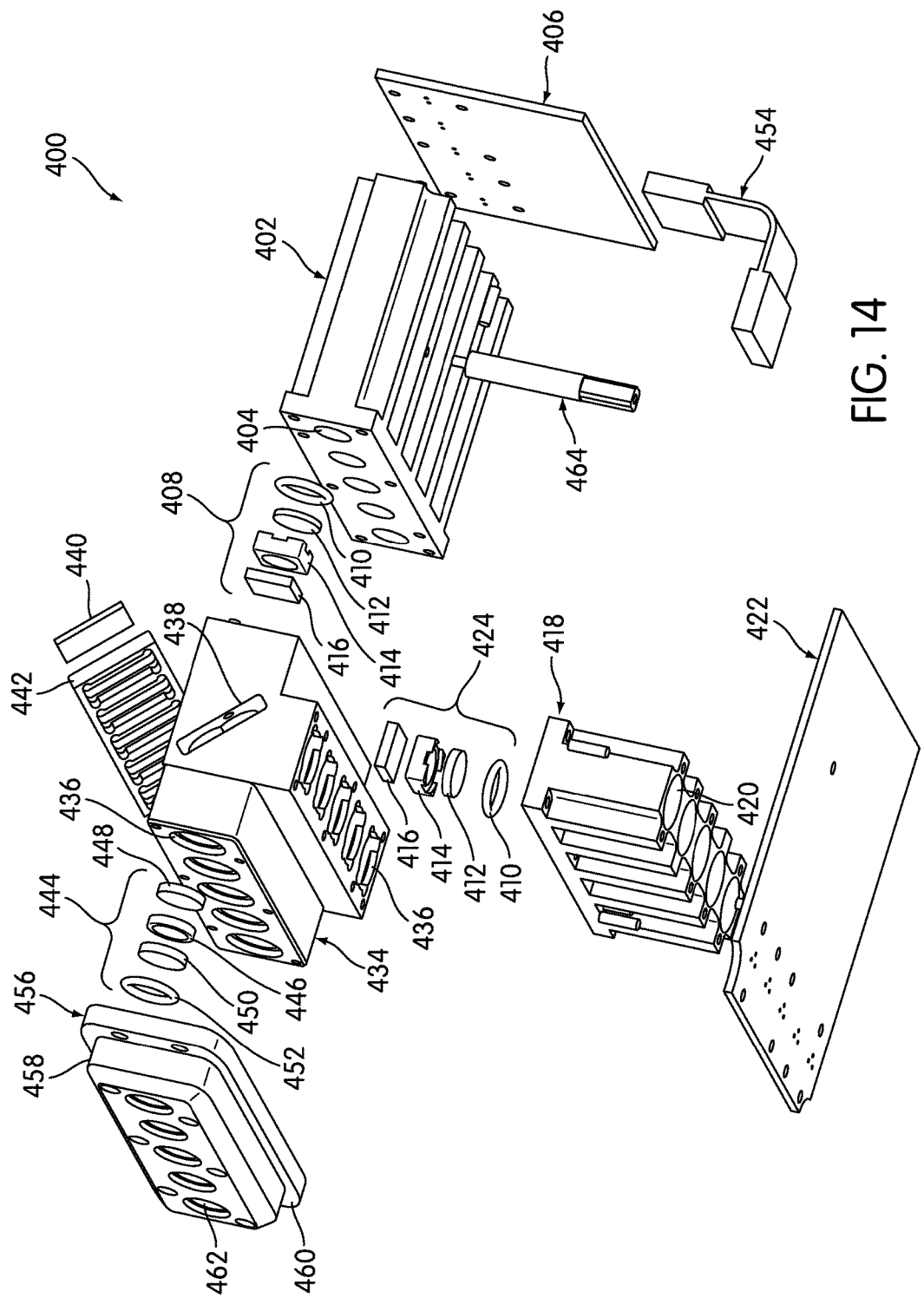
FIG. 14 is an exploded perspective view of the signal detector.

As shown in FIGS. 13 and 14, which show a side cross-sectional view and an exploded perspective view, respectively, of the signal detector, the excitation housing 402 includes five excitation channels 404. An excitation light source 405, such as a light-emitting diode ("LED") coupled to the excitation PCB 406 is located at the end of each excitation channel 404. Similarly, the detector housing 418 includes five emission channels 420, and a detector element, or optical signal detector, 423, such as a photodiode, is provided in each emission channel 420 and is coupled to the detector PCB 422. A standoff 464 is mounted between the excitation housing 402 and the detector PCB 422 at a distance from the detector housing 418 to provide additional stability for the detector PCB 422.

Within each individual channel of each detector 400 there are two optical paths defined by excitation optics and emission optics disposed, at least partially, within the excitation and emission channels, respectively. As described in more detail below, the excitation optical path begins with an LED as the light source, which light is collimated by an excitation lens and then filtered through an excitation filter. The filtered light passes upward through a beam splitter and is focused onto a receptacle vessel 162 by objective lenses between the receptacle vessel 162 and the beam splitter. The emission optical path originates from the light emitted by the contents of the receptacle vessel 162, which is collimated by the objective lenses as the light passes toward the beam splitter and is reflected by the beam splitter toward the emission channel. Within the emission channel, after being filtered through an emission filter, the light is focused by an emission lens onto the detector element 423, such as a photodetector.

The various optical elements of the detector 400 are located in the optics housing 434. For each excitation channel 404 of the excitation housing 402, the optics housing 434 contains excitation optics 408, for each emission channel 420 of the detector housing 418, the optics housing 434 contains emission optics 424, and for each detector opening 462 of the interface cap 456, the optics housing 434 contains input/output optics 444. The excitation optics 408, emission optics 424, and input/output optics 444 are disposed within optics channels 436 formed within the optics housing 434.

The excitation optics comprises an optical focus and filter assembly and include an excitation lens 412, a lens holder 414, and an excitation filter 416. An O-ring 410 provides a light-tight seal between the excitation housing 402 and the optics housing 434. The excitation filter 416 is selected so as to pass excitation light from the light source 405 within the excitation channel 404 having a desired excitation characteristic (e.g., wavelength).

The emission optics include an emission lens 428, a lens holder 430 and an emission filter 432. An O-ring 426 provides a light-tight seal between the detector housing 418 and the optics housing 434. The emission filter 432 is selected so as to transmit only that portion of a signal emitted by the contents of a reaction receptacle to the detector 423 within the emission channel 420 having a desired signal characteristic (e.g., wavelength).

The input/output optics 444 include a first objective lens 450 and a second objective lens 448 with a spacer ring 446 disposed therebetween. An O-ring 452 provides a light-tight seal between the interface cap 456 and the optics housing 434.

The detector 400 further includes dichroic beam-splitters comprising dichroic beam-splitter elements 440 held within a beam-splitter frame 442 which is inserted into a beam-splitter opening 438 of the optics housing 434. A beam-splitter 440 is provided for each excitation channel 404 and corresponding emission channel 420. The beam-splitter 440 is selected so as to pass excitation light having a prescribed excitation wavelength in a straight optic path from the excitation channel 404 and to deflect emission light from the contents of the receptacle 162 having a prescribed detection wavelength toward the detection channel 420.

Figure 19:
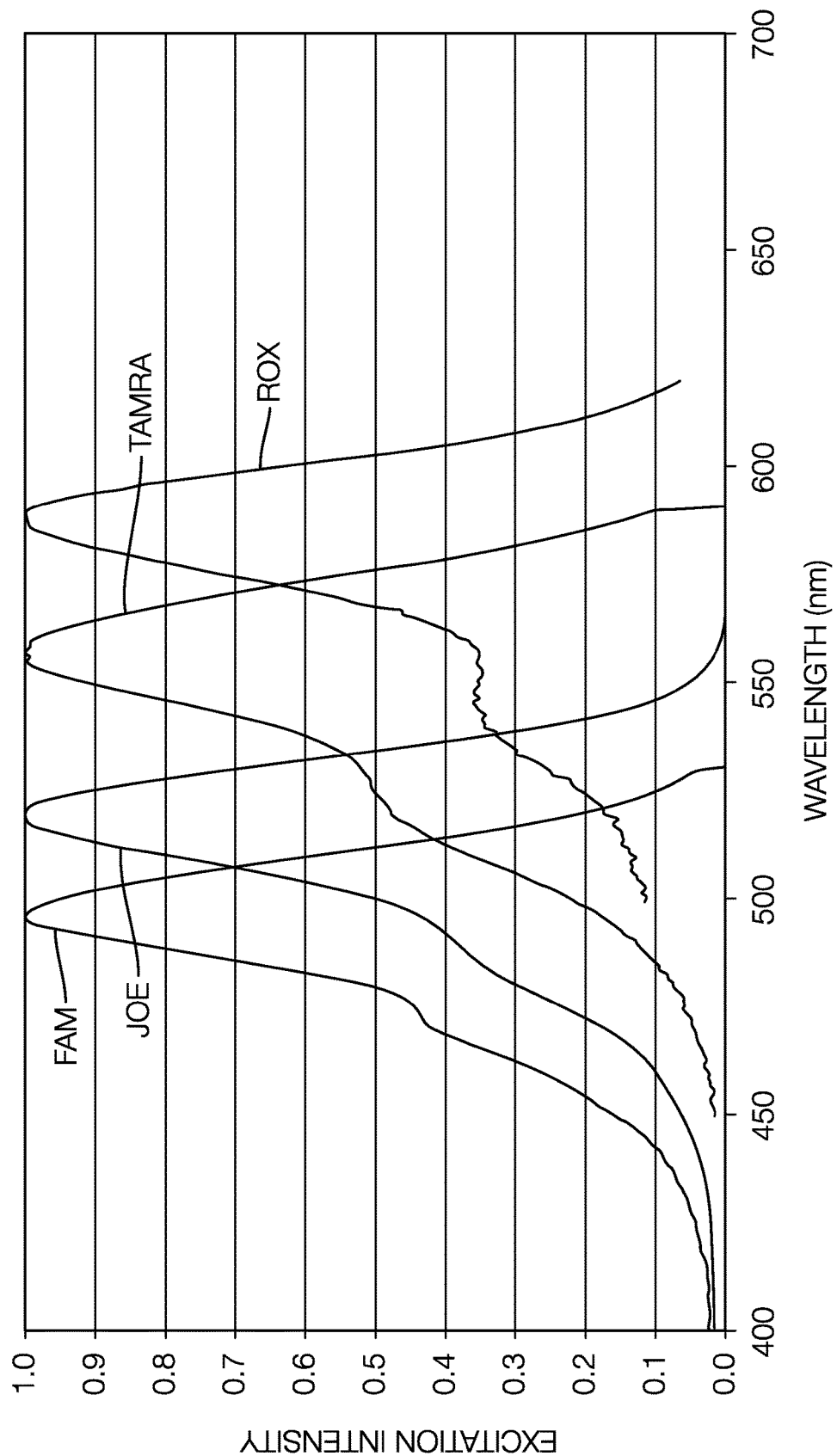
FIG. 19 is a graph showing excitation spectra of preferred amplification detection dyes.
Figure 20:
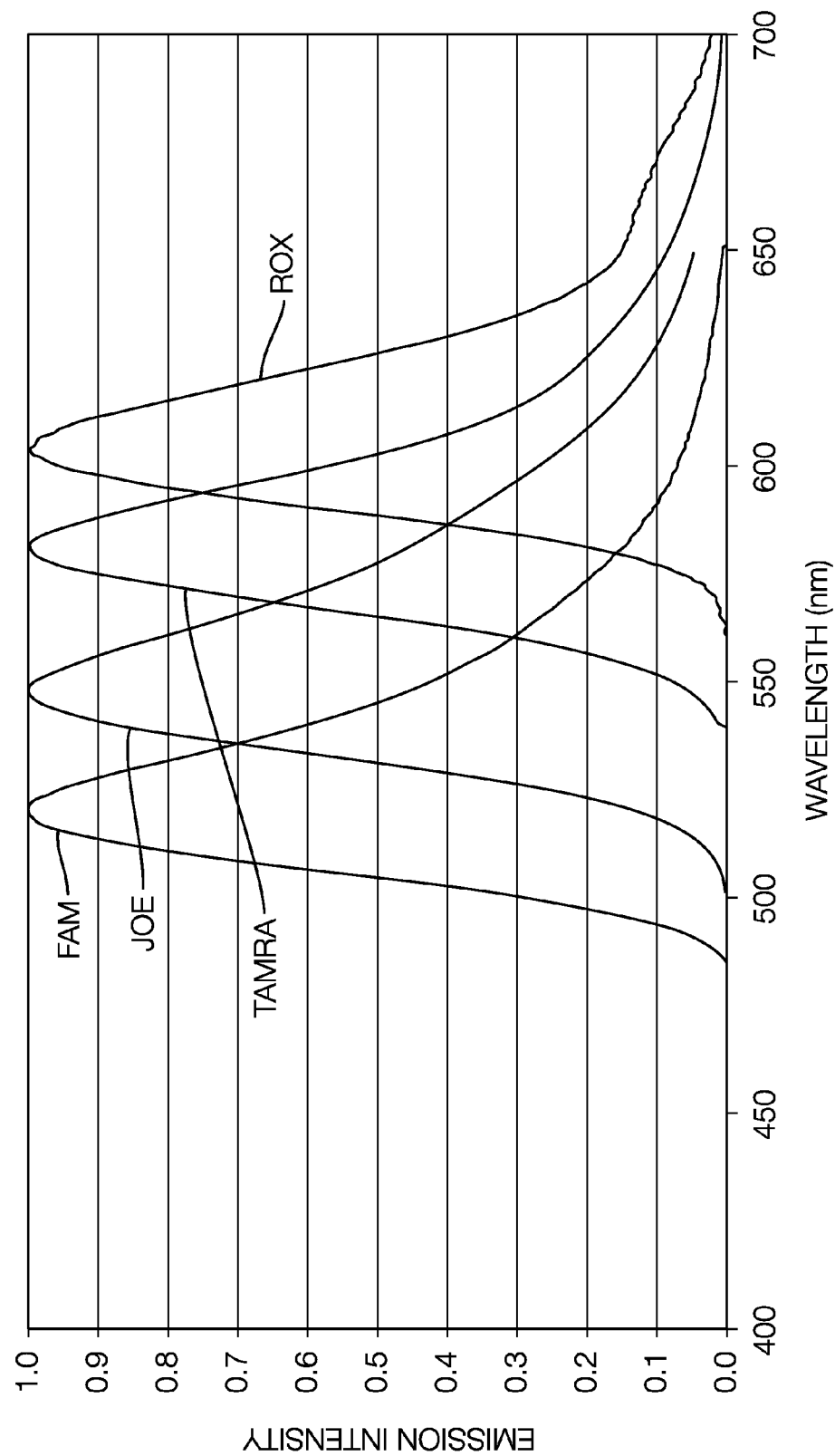
FIG. 20 is a graph showing emission spectra of preferred amplification detection dyes.
Figure 21:
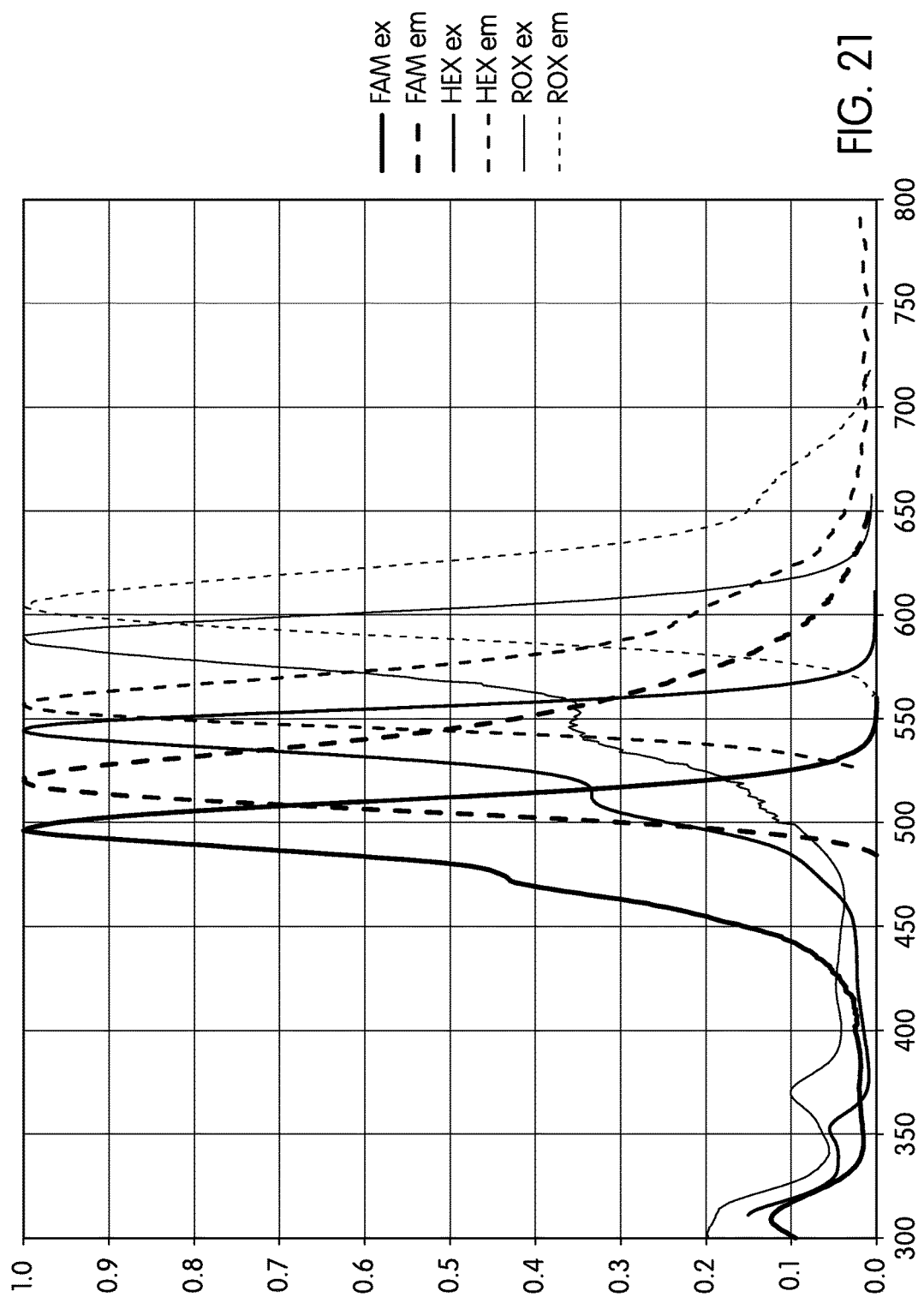
FIG. 21 is a graph showing excitation and emission fluorescence spectra for FAM, HEX, and ROX dyes.

In one embodiment, the signal detector comprises a fluorometer configured to excite a fluorescent dye of a specific wavelength (i.e., color), by directing an optical excitation signal of a specified, associated excitation wavelength at a receptacle containing a sample with which the fluorescent dye is mixed, and to detect an emission signal having a wavelength corresponding to the wavelength, or color, of the specific dye. Different fluorescent dyes are excited at different wavelengths. In one multiplex application of the present invention, suitable dyes include the rhodamine dyes tetramethyl-6-rhodamine ("TAMRA") and tetrapropano-6-carboxyrhodamine ("ROX") and the fluorescein dyes 6-carboxyfluorescein ("FAM") and, each in combination with a DABCYL quencher. Other suitable dyes include 5'-hexachlorofluorescein phosphoramidite ("HEX"), and 2',7'-dimethoxy-4',5'-dichloro-6-carboxyfluorescein ("JOE"). The normalized excitation spectra of FAM, JOE, TAMRA, and ROX dyes are shown in FIG. 19. FIG. 20 shows the normalized emission spectra of the FAM, JOE, TAMRA, and ROX dyes. Because the preferred dyes are excited at different wavelengths, each signal detector 400 is preferably tailored to emit an excitation light at or near the desired excitation wavelength (i.e., color) for the particular dye that the fluorometer is intended to detect. Accordingly, component selection for the detector/fluorometer will, in many instances, be governed by the particular dye for which the signal detector 400 is intended. For example, with respect to the light source 405, the particular LED selection will depend on the dye for which the fluorometer is intended. As shown in FIG. 21, which shows normalized excitation and emission fluorescence versus wavelength for FAM, HEX, and ROX dyes, the HEX excitation wavelength band partially overlaps with FAM emission wavelength band, and the ROX excitation wavelength band partially overlaps with HEX emission wavelength band. See also Table 1 below.

The detectors 400 are identical in design and components, with the exception of components that are dye-specific. The components that are dye-specific include the light source 405, the excitation filter 416, the emission filter 432, and the beam splitter 440.

The following table provides specifications for a selection of filters for different types of dyes:

Filter Specifications

TABLE 1

| Description | Center Wavelength (nm) | Bandwidth (nm) | Dimensions (mm) | Thickness |
|---|---|---|---|---|
| FAM Excite Filter | 460 | 60 | 8.9 × 8.9 square | 2 |
| FAM Emission Filter | 525 | 30 | 8.9 × 8.9 square | 2 |
| FAM Short Wave Pass Dichroic | | | 10 × 14.8 rectangular | 1.05 |
| HEX Excite Filter | 535 | 22 | 8.9 × 8.9 square | 2 |
| HEX Emission Filter | 567 | 15 | 8.9 × 8.9 square | 2 |
| HEX Short Wave Pass Dichroic | | | 10 × 14.8 rectangular | 1.05 |
| ROX Excite Filter | 585 | 29 | 8.9 × 8.9 square | 2 |
| ROX Emission Filter | 632 | 22 | 8.9 × 8.9 square | 2 |
| ROX Short Wave Pass Dichroic | | | 10 × 14.8 rectangular | 1.05 |

The following table provides specifications for a selection of lenses for different types of dyes:

Lens and O-Ring Specifications

TABLE 2

| Dye = FAM, HEX, ROX | | |
|---|---|---|
| Part No. | Description | Vendor |
| NT47-475 | Emission Lens | Edmund or Ross |
| NT47-477 | Excitation Lens | Edmund or Ross |
| NT47-476 | Objective Lens | Edmund or Ross |
| 94115K478 | O-ring | McMaster |

Table 3 shows certain preferred characteristics of exemplary blue, green, and amber LED:

LED Specifications

TABLE 3

| Characteristic | Blue | Green | Amber |
|---|---|---|---|
| Chip Size | 24 mil | 11 mil | 25 mil |
| Dominant Wavelength | 462 nm | 533 nm | 590 nm |
| Radiant Flux | 4 mW | 2 mW | 1.2 mW |
| Max DC forward current | 200 mA | 50 mA | 150 mA |

Note that in the illustrated embodiment, the beam splitter 440 passes the excitation light and reflects the emission light. Since the excitation channel is longer than the emission channel, this arrangement provides a narrow profile for the housing of the signal detector 400, thereby maximizing the number of detectors 400 that can be positioned at angular intervals beneath the incubator 200, as shown in FIG. 10. Spatial limitations and preferences may be accounted for in designing the excitation and emission channels, which can be interchanged from the format depicted in FIG. 10. In such an embodiment a beam splitter that reflects the excitation light and passes the emission light could be used.

Figure 22:
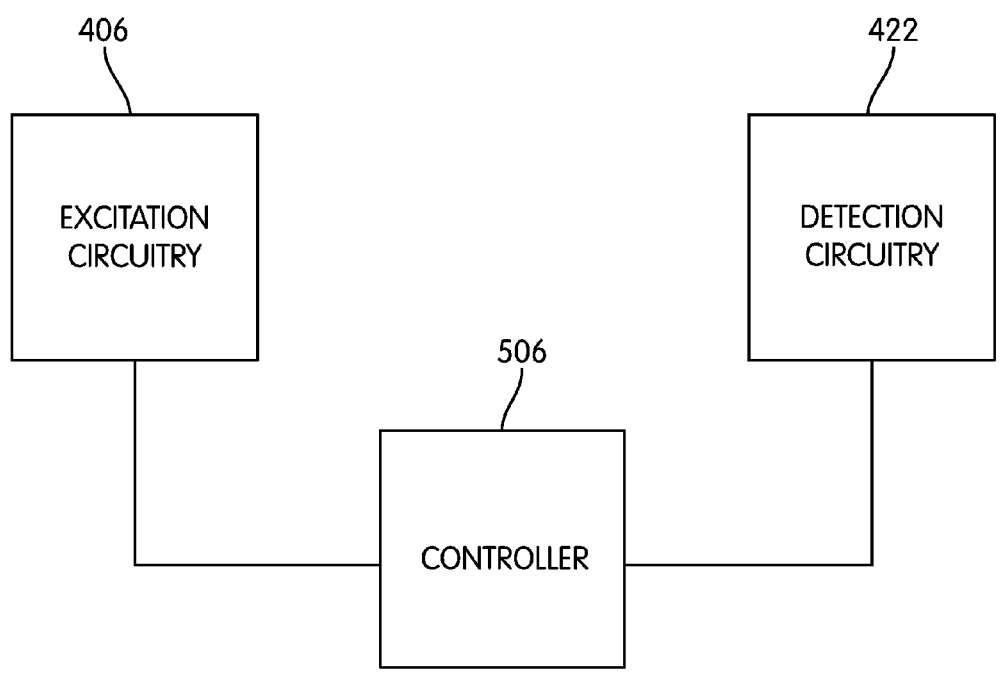
FIG. 22 is a block diagram schematically illustrating excitation and detection architecture.

The data acquisition system and process for acquiring, storing, and processing signal data emitted by the contents of the MRDs 160 can be described at a high level with reference to FIG. 22. In general, the system and process include three components: excitation 406, detection 422, and control 506. The Excitation branch, or circuitry, 406 generates a power signal to control the light source (e.g., an LED) to generate an excitation light signal. The detection branch, or circuitry, 422 includes a light detector (e.g., a photodiode) that converts photons of light that impinge on the detector to a current. The control branch, or controller, 506 drives and controls the excitation circuitry 406 and processes the emission data generated by the detection circuitry 422.

Figure 23:
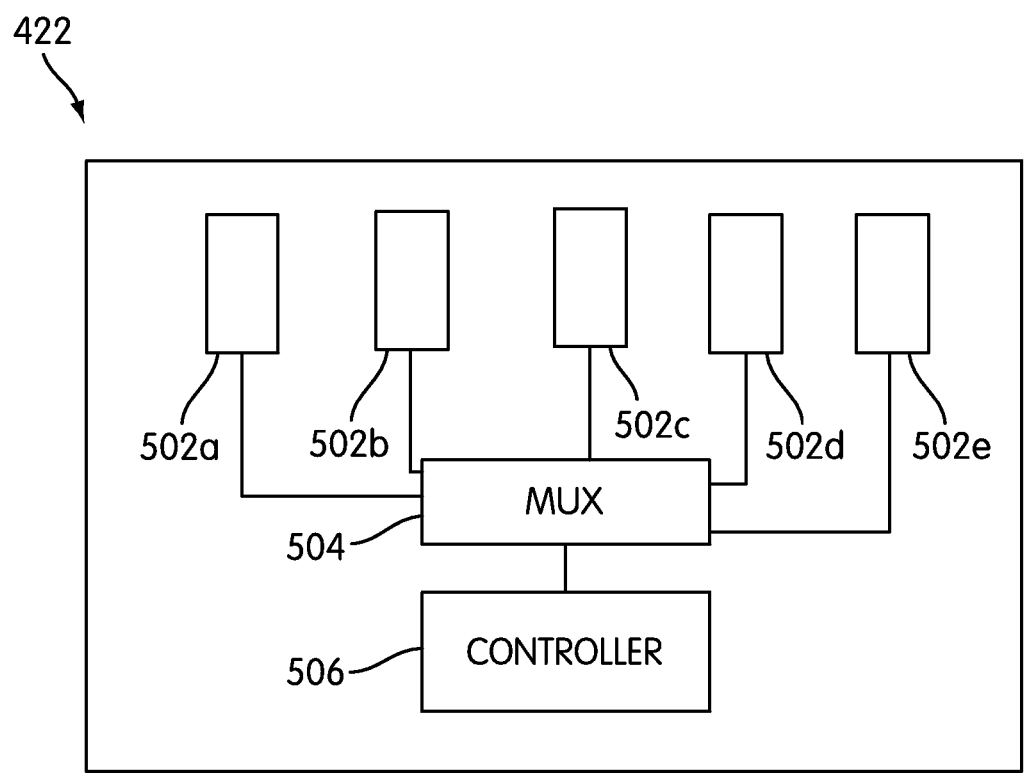
FIG. 23 is a block diagram schematically illustrating an arrangement of detection circuitry.

FIG. 23 depicts a logical block diagram of an arrangement of the detection circuitry 422. The detection circuitry on the detector PCB 422 can include detector circuits 502a-502e, which are configured to detect fluorescent light and to convert the detected light to a voltage signal that can be processed by the controller 506. The output from the detector circuits 502a-502e can be connected to controller 506 either directly or through a multiplexer 504, as is shown in FIG. 23.

Figure 24:
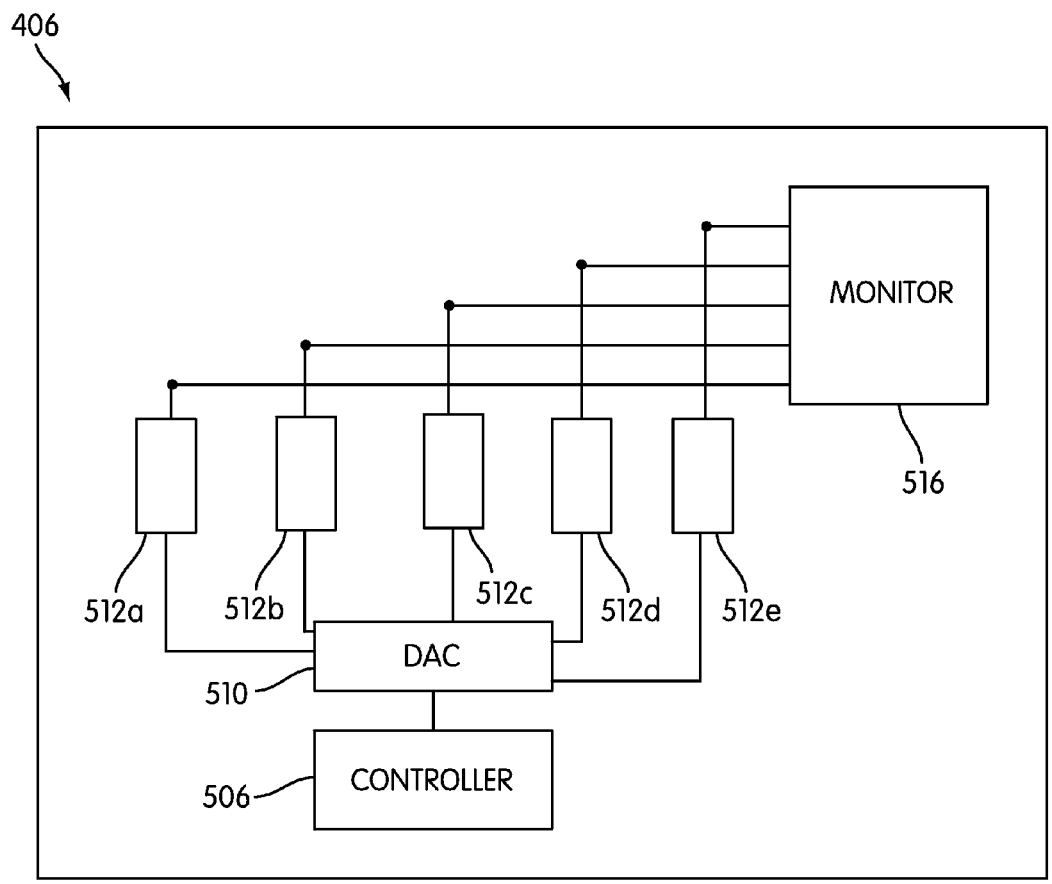
FIG. 24 is a block diagram schematically illustrating an arrangement of excitation circuitry.

FIG. 24 depicts a logical block diagram of an arrangement of the excitation circuitry. As shown in FIG. 24, which is a block diagram schematically illustrating an arrangement of excitation circuitry, excitation circuitry can include the controller 506 and a digital to analog converter (DAC) 510. The excitation circuitry on the excitation PCB 406 includes excitation circuits 512a-512e for driving each excitation source 405 of each excitation channel 404. The excitation circuits 512a-512e are driven by a digital to analog converter (DAC) controlled current source. The current source is a voltage to current amplifier that controls the current flowing through the excitation source 405.

A monitor 516 can be connected to excitation circuits 512a-512e to facilitate process control of the excitation voltage. Checking the voltage across the LED and the current through the LED give a good indication if the LED is functioning correctly. This is a diagnostic capability that can be used in a variety of ways. For example, the LED could be checked at power-on, during a self test, so when the fluorometer powers up it could put a known current through the LED, and if the forward voltage of the LED is in an expected range, then the system would pass the self test. These values could also be checked during an assay to monitor correct functioning of the LED.

Figure 25:
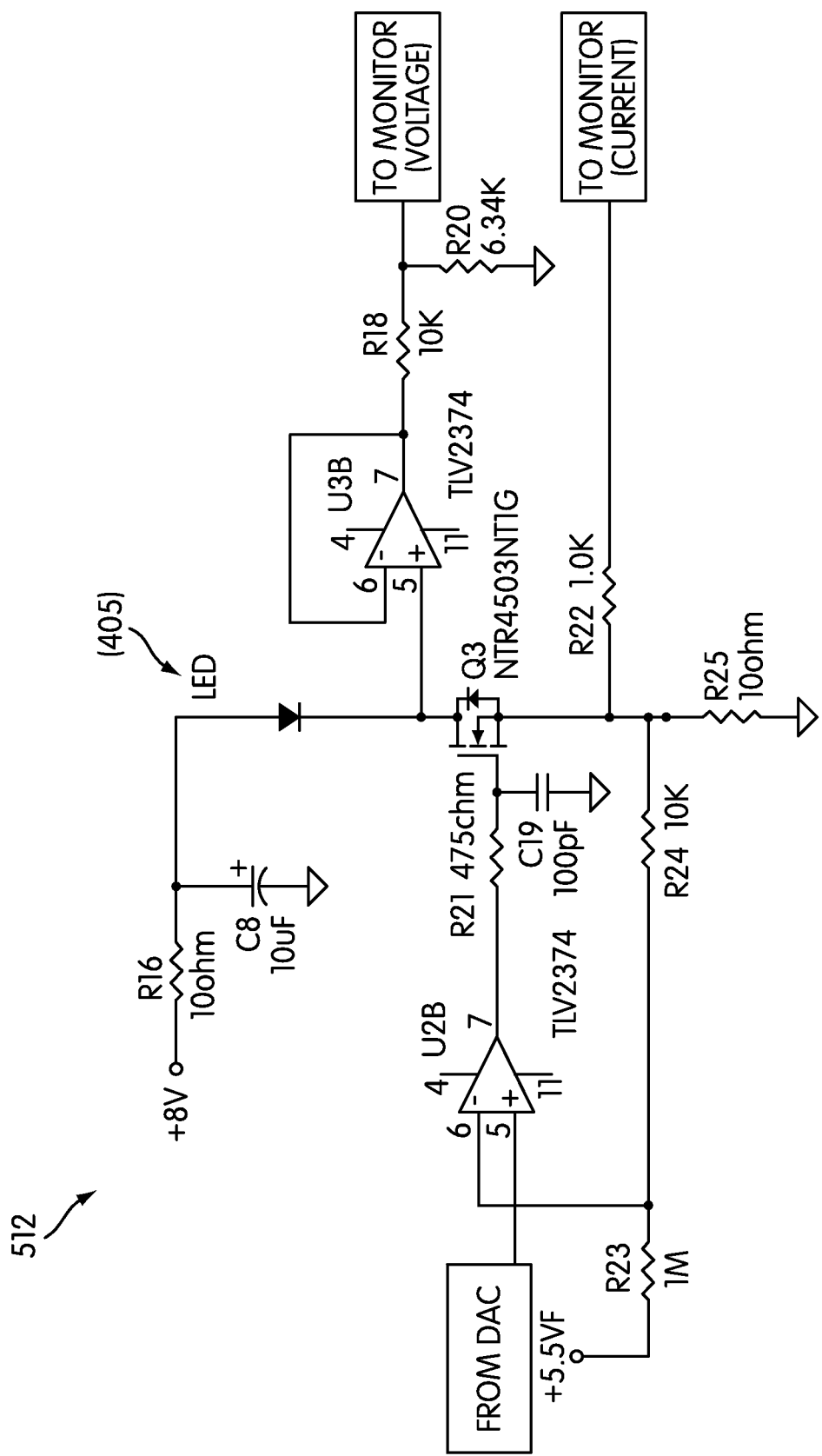
FIG. 25 is a circuit diagram illustrating a fluorometer excitation circuit.

According to embodiments of the invention, each of the LEDs (corresponding to excitation source 405) in circuits 512a-512e can be driven by a digital to analog converter controlled current source, as shown in FIG. 25, which is a circuit diagram illustrating a fluorometer excitation circuit. The current source can be a voltage to current amplifier that controls the current flowing through the LED (corresponding to excitation source 405).

In addition to performing the function of driving a computer controlled current waveform through the LED, the current source shown in FIG. 25 allows for process control based on LED current and voltage. The output of the circuit formed by U3B is a monitor of the voltage across the LED and can be digitized by monitor 516 using an A/D converter. Similarly the output of R22 (the side away from transistor Q3) can be used to monitor the current passing through the LED and similarly digitized by an A/D converter located in monitor 516. The current through the LED is monitored for diagnostic purposes, as described above.

Figure 26A:
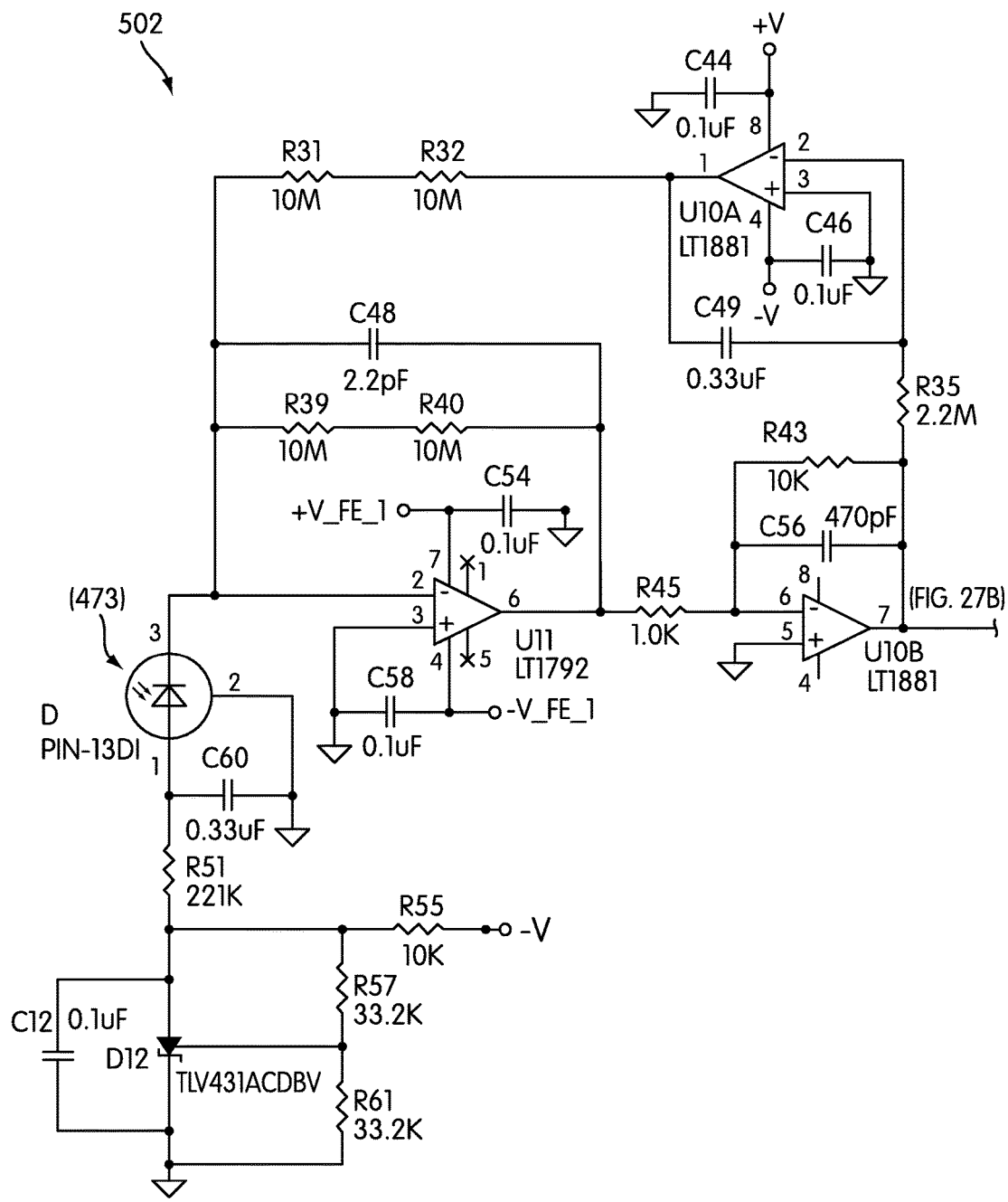
FIGS. 26A and 26B are two parts of a circuit diagram illustrating a fluorometer detection circuit.
Figure 26B:
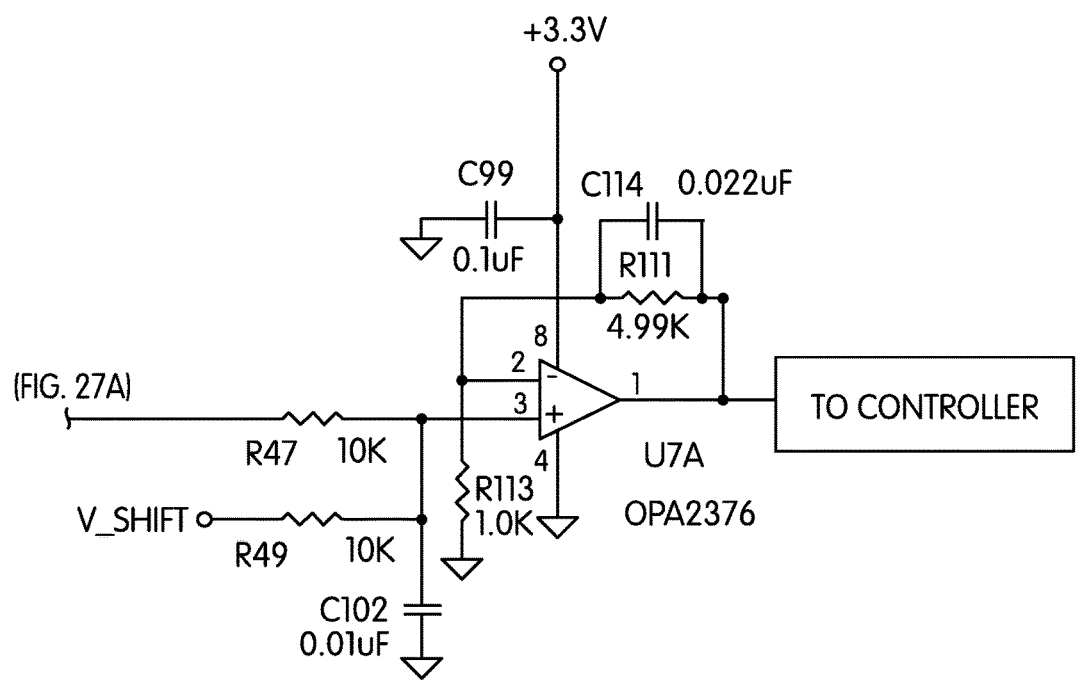

The detector circuits 502a-502e could be configured as shown in FIGS. 26A and 26B. Each detector circuit 502 includes a pre-amplifier circuit, which includes U11, and the amplifier formed by pins 5-7 of U10B. The pre-amplifier circuit receives current from the photodiode D 473 (corresponding to detector element 423) and converts it to an amplified voltage. As shown, the amplifier that includes pins 1-3 of U10A provides a bias current to compensate for the electrical current out of photodiode D caused by un-modulated ambient light incident on the photodiode D.

Amplifiers U11 and U10B form the first two stages of amplification of the current signal (corresponding to the emission signal) from the photodiode D (423). C54, C44, and C58 provide power supply bypassing/filtering to the amplifiers. C12, D12, R55, R57, and R61 form a filtered power supply that biases the anode of the photodiode D. Feedback resistors R31 and R32 convert electrical current from the photodiode D into a voltage while C48 provides filtering for higher frequency signals. The voltage divider formed by R43 and R45 provides a voltage gain of 10 in the next pre-amplification state while capacitor C56 provides additional low pass filtering.

The detector circuits 502a-502e are configured to use a level shifter formed by U7A. Though not wishing to be bound by theory, the purpose of the level shifter is to move the zero level of the pre-amp up to the middle range of a unipolar analog to digital converter. This allows the use of A/D converters employed by certain microcontrollers so that an additional A/D converter is not required.

During operation, while multiple receptacles (e.g., MRDs 160) are being processed within the incubator 200 and one or more signal detectors 400 are measuring the intensity of signal emissions from the receptacles carried on the receptacle carrier 242, it is desirable to periodically self-check the signal detectors to detect any failure or deteriorated performance. Such a failure or performance deterioration can affect the accuracy of test results, which hinge on measurement of optical emissions from the sample tubes. In general, such self-checking is performed in accordance with aspects of the present invention by moving an optical reference standard 250 (e.g., a fluorescent reference standard) into optical communication with each channel of each signal detector 400 (or in the case of a non-stationary detector, moving the detector into optical communication with an optical reference standard), measuring the optical emission intensity from the reference standard, and comparing the measured intensity to an expected intensity. A difference between the measured and expected intensities that exceeds a threshold may be indicative of failure or deteriorated performance of the signal detector. In the case of a stationary detector, each reference standard may be carried on a support with respect to the stationary signal detectors 400 to periodically place the reference standard in optical communication with a channel of the signal detector. "Optical communication" in the present context refers to positioning the optical reference standard in a position with respect to a channel of the signal detector, or positioning a channel of the signal detector in a position with respect to the optical reference standard, such that the signal detector is able to detect an optical emission from the standard. In the illustrated embodiment, as shown in FIGS. 4, 5, 6, and 9, optical reference standards 250 are provided on selected outer spokes 264 of the lower disk 256 of the receptacle carrier 242. These standards are positioned and oriented in this embodiment such that as the carrier 242 rotates within the incubator 200, one or more reference standards 250 can be moved into a position with respect to a channel of a signal detector 400 that will enable the signal detector 400 to measure the optical emission from the standard 250. In one embodiment, the optical reference standard is a fluorescent reference standard made from a fluorescent material that will provide an elevated relative fluorescent signal when the standard is placed in optical communication with a channel of a signal detector 400. That is, the fluorescent standard will generate a sufficiently high fluorescent emission signal that failure or deteriorated performance of a signal detector will manifest itself in a detectable change in the measured fluorescent emission intensity from the standard.

In the illustrated embodiment, each fluorescent reference standard 250 comprises a single fluorescent plastic disk secured onto an outer surface of an outer spoke 264 of the lower disk 256 as a self-check target for each of the five channels of the signal detector 400. Each group of five reference standards 250 (corresponding to the number of channels of each signal detector 400) on one outer spoke 264 comprises a reference standard set, and the number of reference standard sets preferably corresponds to the number of signal detectors 400 positioned beneath the incubator 200 so that all of the signal detectors can be self-checked simultaneously. That is, in one embodiment, each reference standard set corresponds to, or is associated with, one signal detector. In other embodiments, reference standard sets are positioned relative to their corresponding signal detector so that one or more, but less than all, signal detectors can be self-checked while one or more other signal detectors are measuring signal emissions from samples.

By integrating the reference standard into a support structure, such as the receptacle carrier 242, within the incubator 200, the signal detector(s) 400 can be self-checked during operation of the incubator 200, including during the real-time monitoring of amplification reactions within the incubator. Thus, the self-check procedure can be performed within the closed system of the incubator without requiring that normal operation of the incubator be interrupted to permit the signal detector(s) to be checked for proper operation.

Suitable materials for the fluorescent standards 250 frequently comprise consumer-grade fluorescent plastic sheets from which disks (of, e.g., 3.5 mm diameter) can be cut or stamped and secured to the outer spokes 264. The fluorescent plastic discs may be secured to the spoke by a suitable adhesive and/or pressed into a friction fit within a, for example, circular hole formed in the spoke 264. Forming holes in the outer spokes 264 for receiving the reference standards 250 while machining the lower disk 256 of the receptacle carrier 242 will simplify the later process of securing the reference standards 250 to the disk 256 and will ensure that the references standards 250 are properly located on the disk 256. Suitable plastic sheets include fluorescent plastic sheet available from McMaster-Car (Part No. 85635K412, color Amber) manufactured by Reynolds Polymer and Acrycast Cell Cast Acrylic Sheet (Part No. 2422, color Amber). Preliminary tests indicate that the McMaster-Car Amber plastic is a preferable reference standard material for self-checking fluorometers configured to detect ROX dyes, and the Acrycast Cell Cast Acrylic amber is a preferable reference standard material for self-checking fluorometers configured to detect FAM and HEX dyes. Other colors may be suitable for reference standards, such as blue, pink, and green.

The colors, or other emission characteristics, of reference standards of different reference standard sets may all be the same, or different colors may be used in different reference standard sets for self-checking fluorometers, or other signal detectors, configured to detect different colors. Furthermore, all the reference standards in each reference standard set may be the same color, or different colored reference standards may be used in a reference standard set if the different channels of the signal detector are configured to detect different colors.

One of skill in the art may appreciate that a variety of materials exist that have that have overt fluorescent characteristics, producing strong fluorescence signals when excited with appropriate light wavelengths (e.g., the fluorescent plastics described above). Many more materials have residual fluorescent characteristics, which may be referred to as autofluorescence or natural fluorescence. These residual fluorescent characteristics are generally weak signals and may have a wide spectrum of excitation and emission wavelengths. In the context of the present description, these materials include certain plastics or metals present in the system, or designed into the system. For example, MRDs of the present disclosure may be comprised of a polymeric material that has residual fluorescent characteristics. Similarly, portions of an incubator, spokes on a carousel, fiber optic materials such as plastic or glass fibers, or a component of another transport mechanism may be comprised of a material that has residual fluorescent characteristics. In certain embodiments where fluorometers are being monitored for failure, these materials having residual fluorescence characteristics can comprise the fluorescent reference standards of the present disclosure. Generally, however, the weaker residual fluorescent signal must have enough strength to be identified by the fluorometer to be effective as a fluorescent reference standard. Frequently this weaker residual fluorescent signal is strong enough for detection without having to adjust the strength of the excitation signal or the gain in the system that are used to evaluate test samples. The appropriate materials are determined for each fluorometer channel based on the excitation and emission characteristics of the material. In these embodiments, each fluorometer channel (e.g., FAM, ROX, HEX, etc.) may require a different fluorescent reference standard, but two or more channels may be able to share a single material if the emission characteristics of the material are sufficiently distinguishable using the different excitation wavelengths. For example, one fluorometer channel may use an MRD as its fluorescent reference standard, another fluorometer channel in the system may utilize a spoke as its fluorescent reference standard, and still another fluorometer channel may utilize a hole or indentation drilled in a spoke as its fluorescent reference standard. In another embodiment, fiber optic materials such as fibers utilized to carry an excitation and/or emission signal (e.g., light pipes) may be utilized as the fluorescent reference standard. Though plastic fiber optic materials are known to have higher levels of autofluorescence, in general the fiber optic materials, e.g., plastic, glass, or another type of fiber material, may be chosen based on its autofluorescence characteristics and the fluorometer requirements in the system. One of skill in the art can adjust the choice of fluorescent reference standards based on excitation and emission wavelengths, and signal strengths based on the disclosure provided herein.

Figure 15:
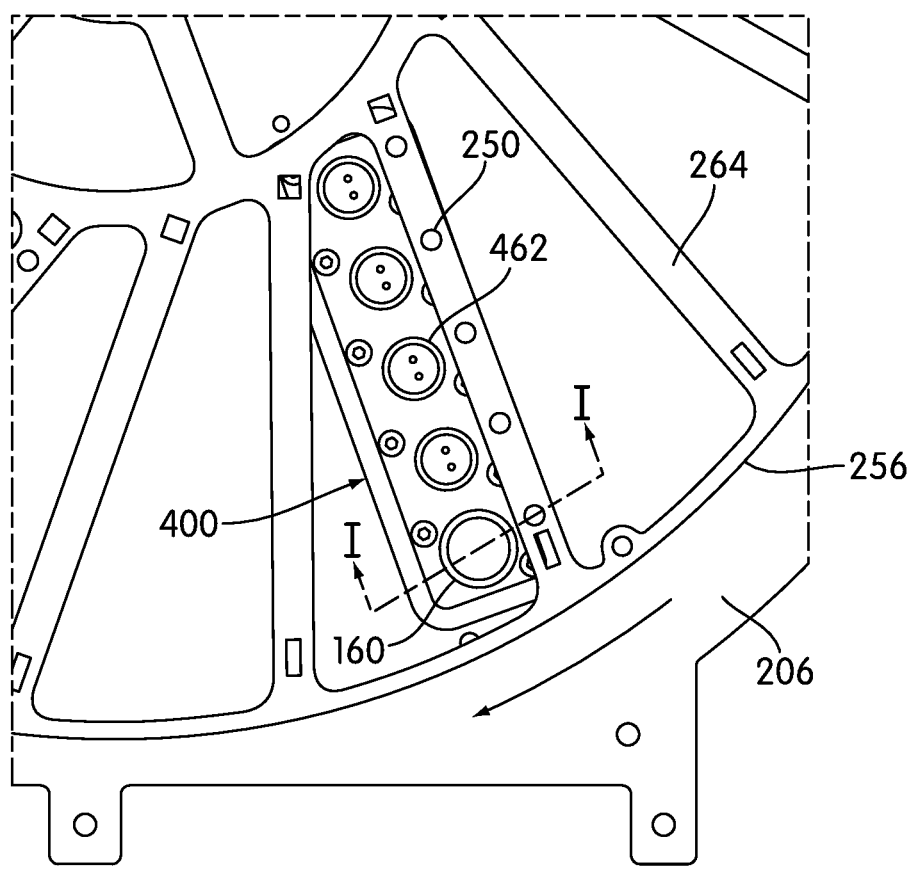
FIG. 15 is a partial top plan view of a lower disk of the receptacle carrier carousel of the incubator, showing alignment of a multiple receptacle device carried on the receptacle carrier with a signal detector positioned below the receptacle carrier and the relative orientations of fluorescent standards mounted on the lower disk relative to the signal detector.

In one embodiment, the reference standards 250 of each reference standard set are arranged in a linear configuration on one outer spoke 264. As shown in FIG. 15, however, in the illustrated embodiment, the outer spokes 264 are not arranged in a radial orientation with respect to the lower disk 256. Each signal detector 400 is parallel to the outer spokes 264 and is oriented such that each of its five channels will simultaneously align with one of the receptacle vessels 162 of a MRD 160 positioned above the signal detector 400. Accordingly, because the MRD 160 is carried within the carousel at a position that is adjacent to and parallel with the outer spoke 264, and because the outer spoke and the MRD are not carried in a radial orientation, the five reference standards 250 of each reference set will not simultaneously align with the five channels of a signal detector 400. Therefore, to place each of the reference standards 250 in optical communication with its corresponding channel of the signal detector 400, the carousel must be rotated in five increments to test all five channels of the signal detector. In one embodiment, the carousel must be rotated 4.65 degrees from the position shown in FIG. 15 to place the first reference standard (i.e., the radially outermost reference standard) into optical communication with the outermost channel of the signal detector. Each subsequent incremental rotation required to place the next four reference standards into optical communication with its corresponding channel are shown in the following table.

| Target-spoke position | Angle |
| --- | --- |
| MRD and fluorometer aligned (as in FIG. 15) | 0° |
| Reference target aligned with outermost fluorometer channel | 4.65° |
| Reference target aligned with second fluorometer channel | 5.35° |
| Reference target aligned with third fluorometer channel | 6.25° |
| Reference target aligned with fourth fluorometer channel | 7.6° |
| Reference target aligned with fifth (innermost) fluorometer channel | 9.75° |

Rather than moving the receptacle carrier 242 by each of the small incremental rotations listed above to sequentially place all the channels of all the signal detectors 400 into self-check positions with respect to an associated reference standard 250, in one embodiment, a different channel of each of the signal detectors 400 is self-tested with each revolution of the carousel. Thus, after one revolution of the receptacle carrier 242 during which all receptacle vessels of all the MRDs 160 are interrogated by all the signal detectors 400, the carousel is advanced until one of the channels (e.g., the first channel) of all the signal detectors 400 is aligned with an associated reference standard 250 for a self-check of all the first channels. After a next revolution of the receptacle carrier 242, the carousel is advanced until the next channel (e.g., the second) of all the signal detectors 400 is aligned with an associated reference standard 250 for a self-check of all the second channels. This process is repeated for each subsequent revolution of the receptacle carrier 242 to self-check the third, fourth, and fifth channels of the signal detectors 400. Thus, according to this embodiment, each channel of each signal detector is self-checked once in every five revolutions of the carousel.

Figure 16:
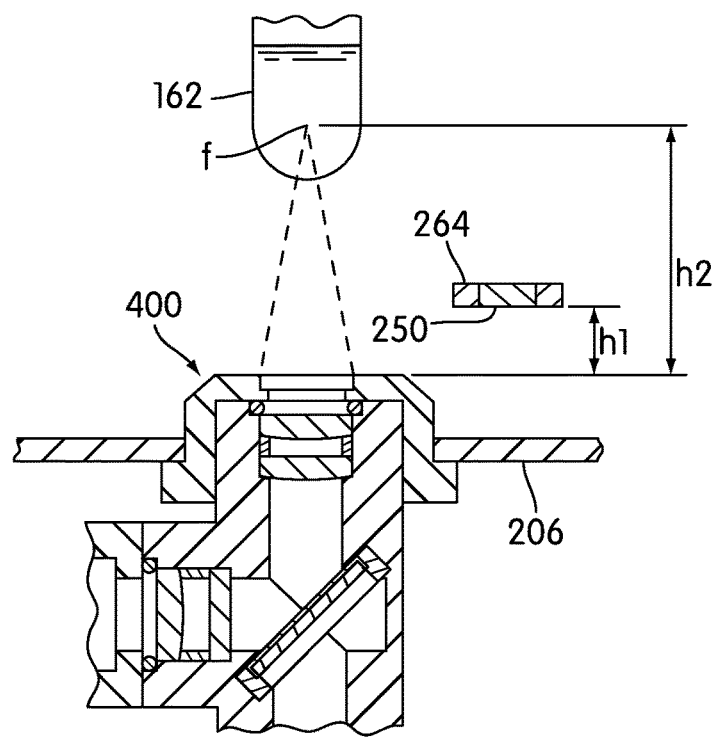
FIG. 16 is a partial side cross sectional view (along ling I-I in FIG. 15) showing a signal detector and a receptacle carried on the receptacle carrier in a detection zone with respect to the signal detector.
Figure 17:
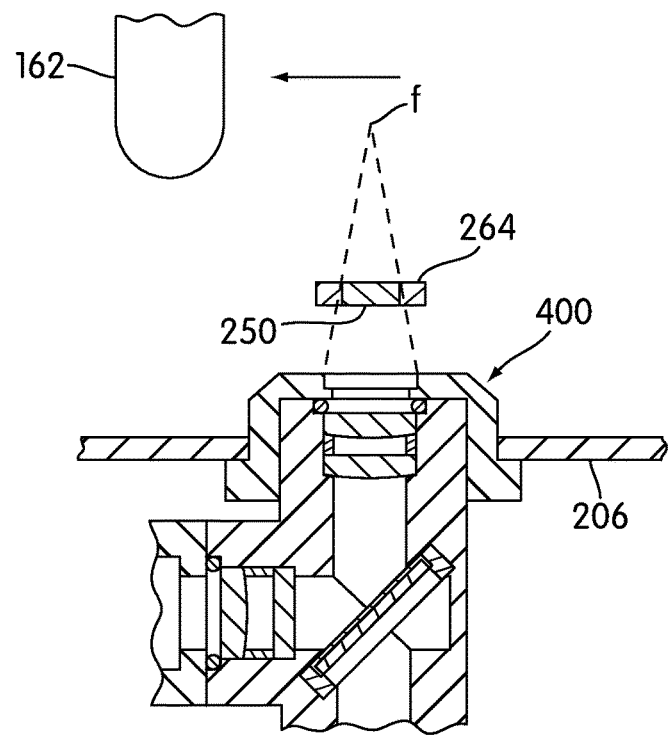
FIG. 17 is a partial side cross sectional view (along ling I-I in FIG. 15) showing the signal detector, the receptacle moved out of the detection zone with respect to the signal detector, and a fluorescent standard moved into optical communication with the signal detector but not in the detection zone with respect to the signal detector.

In one embodiment, the signal detectors 400 are configured so that a receptacle vessel 162 carried on the receptacle carrier 242 will be at an optical focal point of the signal detector 400 when the receptacle vessel 162 is operatively positioned above the signal detector 400. In one embodiment, however, the bottom of each receptacle vessel 162 is positioned above the lower disk 256 on which the reference standards 250 are mounted. Thus, in this embodiment the reference standards 250 are not at the optical focal point of the signal detectors 400. This is illustrated in FIGS. 16 and 17. As shown in FIG. 16, when the receptacle vessel 162 is positioned above the signal detector 400 within the incubator 200, a portion of the receptacle vessel 162 (e.g., approximately within the contents of the receptacle vessel 162) is at a focal point f, or detection zone, at a height $h_2$ with respect to the corresponding channel of the signal detector 400. The reference standard 250, on the other hand, mounted to the outer spoke 264 of the lower disk 256 is at a height $h_1$ that is less than $h_2$ above the signal detector 400. In one embodiment, $h_1$ is 1.0 mm and $h_2$ is 8.5 mm. In another embodiment, $h_1$ is 2.0 mm and $h_2$ is 10 mm. In other embodiments, $h_1$ is 1% to 99% smaller than $h_2$, in other embodiments, $h_1$ is 20% to 80% smaller than $h_2$, and in still other embodiments, $h_1$ is 60% to 90% smaller than $h_2$. Thus, as shown in FIG. 17, after the receptacle carrier 242 rotates in the direction of the lateral arrow to move the receptacle vessel 162 out of the focal point (or detection zone) and place the reference standard 250 into optical communication with respect to the signal detector 400, the reference standard 250 is not at the focal point (i.e., is not in the detection zone) of the corresponding channel of the signal detector 400. Nevertheless, even with the fluorescent reference standards 250 out of focus with respect to the signal detector 400, the inventors have discovered that if the optical emission from the reference standard is suitably robust—meaning that the emission intensity of the reference standard is more intense than the emission intensity of the sample contained within the receptacle vessel 162, which is in focus with respect to the fluorometer—changes in the emission signal from the reference standard due to failure or performance deterioration of the fluorometer can still be adequately detected.

In other embodiments, $h_2$ is less than $h_1$. That is, the support structure on which the reference standards are mounted may be above (or otherwise further from) the focal point f at $h_2$. In such embodiments, $h_2$ may be 1% to 99% smaller than $h_1$, 20% to 80% smaller than $h_1$, or 60% to 90% smaller than $h_1$.

With the reference standard out of focus with respect to the fluorometer, calibrating the fluorometer with the reference standard may be complicated, because it is difficult to obtain precise fluorescent emissions signals from an out of focus reference standard. Thus, the measured fluorescent emission signal from an out of focus reference standard will not frequently be compared to an expected emission signal for the purpose of calibrating the fluorometer. There is likely to be too much variability in measured emission intensity from one measurement to the next. On the other hand, as explained above, even with the reference standard out of focus with respect to the fluorometer, if the reference standard has sufficient emission intensity, it is still possible to confirm proper functioning of the fluorometer by detecting an emission signal of at least a specified intensity level.

In other embodiments, reference standards can be mounted in positions that are in focus with respect to the fluorometer (or the fluorometer can be configured so that the focal point is adjustable) so that precise reference standard emission signals can be obtained and compared to expected signals so that the fluorometer can be calibrated based on the measured reference standard emission signal.

As represented schematically in FIG. 17, the focal cone which terminates at the apex f actually overfills the reference standard 250 at height $h_1$. Thus, reference readings are sensitive to the horizontal positioning of the reference standard 250 because lateral, horizontal movement of the reference standard 250 can cause all or a portion of the reference standard 250 to be positioned outside the focal cone. Thus, in circumstances, such as shown in FIG. 17, in which the focal cone overfills the reference standard 250, positional accuracy of the support on which the reference standard 250 is mounted (e.g., the receptacle carrier 242) is important.

Figure 18:
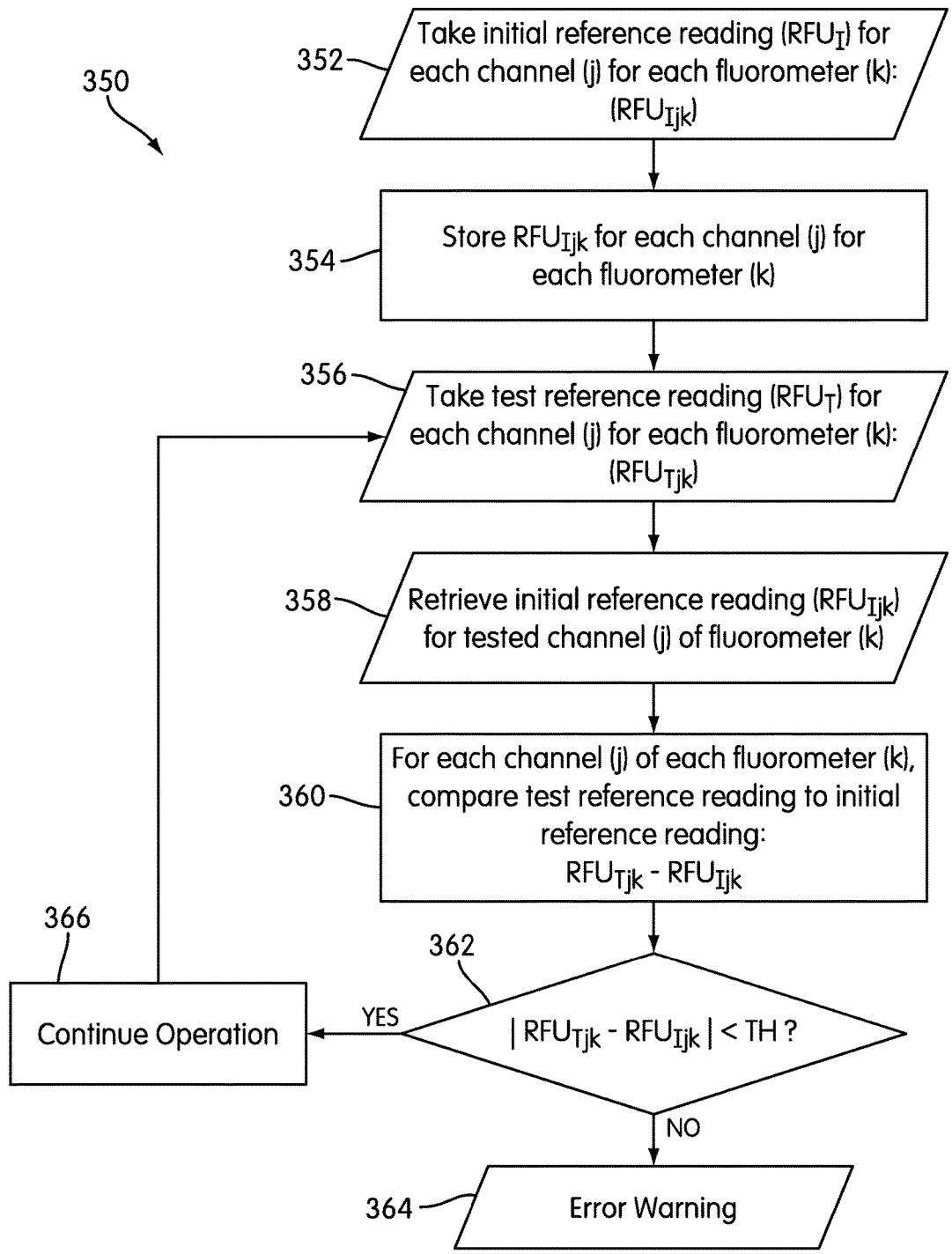
FIG. 18 is a flow chart showing a self-check procedure embodying aspects of the present invention for a fluorometer or other optical signal detector.

An automated, self-check procedure for a signal detector 400 is represented by flow chart 350 shown in FIG. 18. The procedure is performed with the signal detector 400 and the receptacle carrier 242, which are controlled by a computer controller (microprocessor) executing software that includes an algorithm embodying procedure 350 encoded or stored on a computer-readable medium.

At Step 352, an initial, or baseline, reference reading is established for each channel (j) for each signal detector, or fluorometer, (k) by moving the reference standard into optical communication with the channel and measuring an initial optical emission intensity from an associated optical reference standard. Using the example of fluorometers and fluorescent reference standards, a quantifying unit of fluorescent emission intensity may be referred to as a "Relative Fluorescent Unit" ("RFU"), and the initial reference intensity of the $j^{th}$ channel for the $k^{th}$ fluorometer is $RFU_{Ijk}$. The initial, or baseline, reference intensity $RFU_{Ijk}$ can be measured before the signal detector 400 is installed in the incubator 200 or after the fluorometer is installed in the incubator.

At Step 354, the initial reference reading for each channel for each fluorometer ($RFU_{Ijk}$) taken at Step 352 is stored in suitable memory that is accessible by a microprocessor controller.

its excitation signal intensity. As such, the new initial reference reading will account for the excitation signal deterioration, yet provide a useful measure of the operational capacity of the fluorometer (i.e., determine if a failure has occurred).

The typical lifespan of fluorometers that are currently available on the market is, depending on usage frequency and duration, about 5 to 7 years, or about 50,000 hours of operation. Of course, one of skill in the art would appreciate that fluorometer lifespan will vary depending on model, manufacturer, and usage conditions. Over this time LED intensity can, and often does, decrease. The present methods are effective in monitoring the performance of the fluorometer during this gradual decrease in signal intensity witnessed over extended periods of time. For example, Tables 2 and 3 below provide RFU readings of Acrycast Cell Cast Acrylic sheet part No. 2422 color Amber plastic on FAM, HEX and ROX fluorometers (Table 2) and RFU readings of McMaster amber plastic 3.5 mm disks on ROX fluorometers (Table 3).

TABLE 2

|  | Channel 1 | Channel 2 | Channel 3 | Channel 4 | Channel 5 |
| --- | --- | --- | --- | --- | --- |
| No. 5 FAM RTF @20 mA | 7700 | 6900 | 8200 | 8400 | 8700 |
| No. 5 FAM RTF @40 mA | 13400 | 12200 | 14500 | 14800 | 15000 |
| Decrease from 40 to 20 MA | 42.54% | 43.44% | 43.45% | 43.24% | 42.00% |
| No. 10 FAM RTF @20 mA | 8700 | 10300 | 9400 | 10600 | 9700 |
| No. 10 FAM RTF @40 mA | 15200 | 18400 | 16800 | 19100 | 17100 |
| Decrease from 40 to 20 MA | 42.76% | 44.02% | 44.05% | 44.50% | 43.27% |
| No. 5 HEX RTF @20 mA | 4500 | 6500 | 6100 | 7900 | 6900 |
| No. 5 HEX RTF @40 mA | 7700 | 10700 | 10300 | 13000 | 10700 |
| Decrease from 40 to 20 MA | 41.56% | 39.25% | 40.78% | 39.23% | 35.51% |
| No. 10 HEX HEX @20 mA | 7000 | 6900 | 7700 | 8300 | 8100 |
| No. 10 HEX HEX @40 mA | 9950 | 9850 | 11300 | 12200 | 12100 |
| Decrease from 40 to 20 MA | 29.65% | 29.95% | 31.86% | 31.97% | 33.06% |

TABLE 3

|  | Channel 1 | Channel 2 | Channel 3 | Channel 4 | Channel 5 |
| --- | --- | --- | --- | --- | --- |
| No. 5 ROX RTF @20 mA | 8200 | 7600 | 6600 | 10100 | 7600 |
| No. 5 ROX RTF @40 mA | 12900 | 12000 | 10300 | 15900 | 12100 |
| Decrease from 40 to 20 MA | 36.43% | 36.67% | 35.92% | 36.48% | 37.19% |
| No. 10 ROX RTF @20 mA | 9600 | 10800 | 7700 | 8300 | 8200 |
| No. 10 ROX RTF @40 mA | 17000 | 19000 | 13700 | 14700 | 14600 |
| Decrease from 40 to 20 MA | 43.53% | 43.16% | 43.80% | 43.54% | 43.84% |

At Step 356, after an interval of usage of the fluorometer, a test reference reading is taken for each channel (j) for each fluorometer (k) by moving the associated reference standard into optical communication with the channel and measuring an optical emission intensity from the associated optical reference standard. The test reference reading is preferably taken from the same optical reference standard from which the initial reading was taken, since the fluorescent emissions of consumer-grade fluorescent plastics can vary significantly from batch to batch, even for the same nominal color. The test reference intensity of the $j^{th}$ channel for the $k^{th}$ fluorometer is $RFU_{Tjk}$. In this regard, if a reference standard is replaced after a fluorometer has been placed in service; it is preferable to obtain a new initial reference reading for the replaced reference standard. Obtaining a new initial reference reading is important due to the operational lifespan of a fluorometer, which may deteriorate gradually over time in Each channel was tested at two different currents (i.e., 20 mA and 40 mA) to approximate the downward shift in signal intensity that is witnessed over time with a fluorometer. Though a measureable decrease in emission signal intensity with decrease in excitation intensity was observed across all channels, significant levels of fluorescence emissions were detected at the lower current level across all tested fluorophores and fluorometers.

At Step 358, the initial reference reading for the $j^{th}$ channel and the $k^{th}$ fluorometer ($RFU_{Ijk}$) is retrieved from storage, and, at Step 360, the test reference reading is compared to the initial reference reading. In one embodiment, Step 360 is performed by an algorithm that computes the difference between the test reference reading and the initial reference reading for the channel, and in Step 362 the absolute value of that difference is compared to a predetermined threshold value. In one embodiment, a suitable threshold is within a 30% deviation from the initial reference reading. In another embodiment, a suitable threshold is within a 40%-99% deviation from the initial reference reading.

If the absolute value of the difference between the test and initial reference readings is at the threshold or higher, a possible malfunction of the fluorometer is indicated, and, per Step 364 an error warning or other indication of the possible malfunction is provided, and operation of the fluorometer may be interrupted or terminated.

If the absolute value of the difference between the test and initial reference readings is below the threshold, the fluorometer is deemed to be functioning properly, and, per Step 366, operation continues and, as long as the fluorometer continues operation (until a stop condition is reached), periodic self-checks are performed by repeating Steps 356, 358, 360, and 362.

In one embodiment, it is preferred that periodic test reference readings be taken and compared to the initial reference readings at least once every 50 minutes, though the interval can vary significantly in accordance with the user preferences and type of assay being performed. A stop condition may be indicated by completion of the test or assay, a need to stop operation of the instrument to replenish reagents, MRDs, or other disposables, or if, during a fluorometer self-check, the deviation between the test and initial, or baseline, reference readings exceeds the threshold.

Steps 358, 360, 362, 364, and 366 are performed by the computer controller (microprocessor) executing software that includes an algorithm embodying Steps 358, 360, 362, 364, and 366 encoded or stored on a computer-readable medium.

If reference readings are taken every 50 minutes, as mentioned above, and the instrument is operated 12 hours a day for 300 days per year, 25,920 reference readings will be taken after six years of operation. This is equivalent to 14.4 hours of continuous testing at a 2 second sampling rate. Thus, it is important that a reference standard material be selected that is not vulnerable to photo bleaching.

Figure 27:
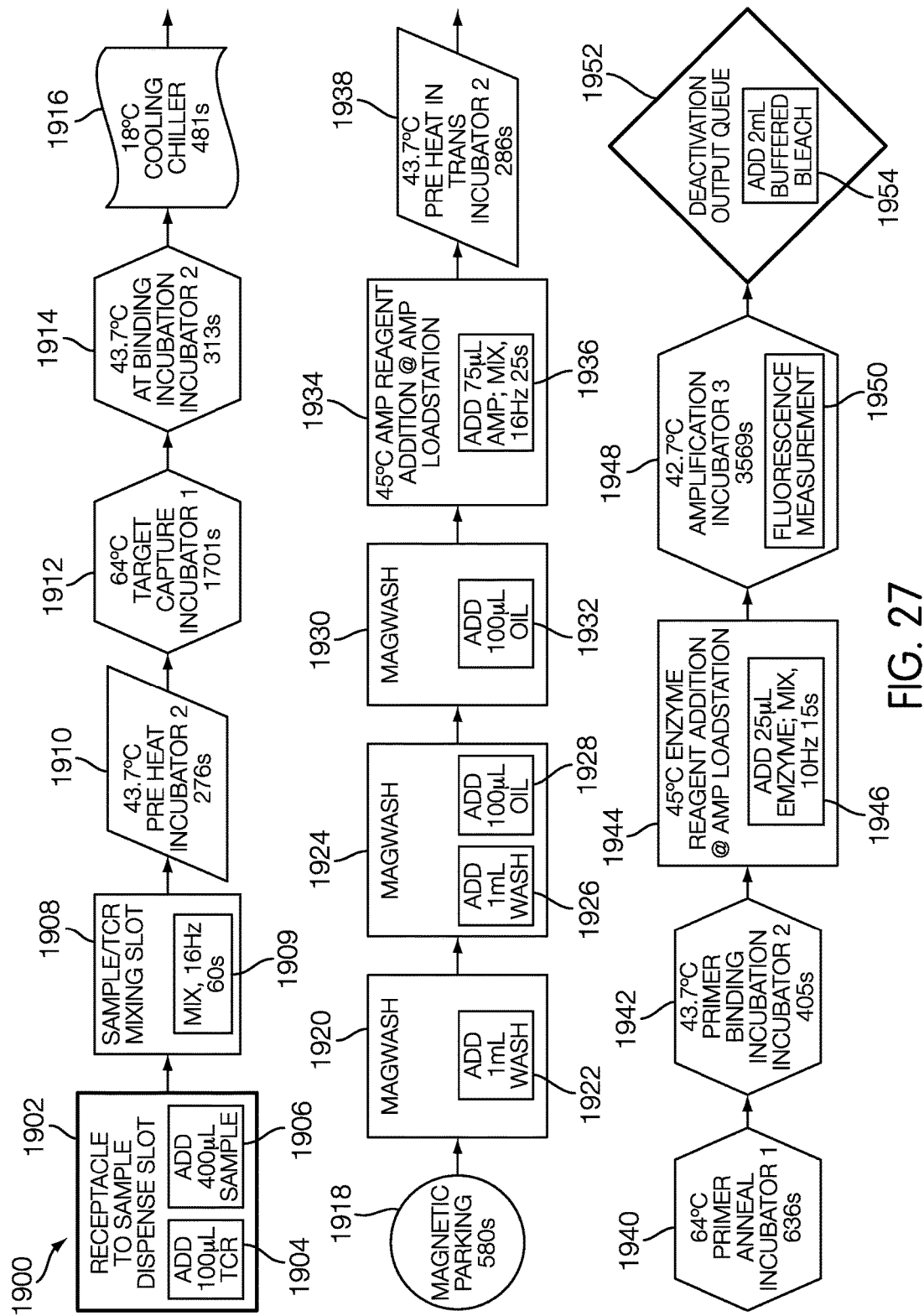
FIG. 27 is a flow chart showing the protocols of an exemplary real-time amplification assay.

The process steps of an exemplary real-time amplification assay procedure 1900 are illustrated in the flow chart shown in FIG. 27. The procedure 1900 is performed by a diagnostic analyzer of which one or more incubators, such as incubator 200, is a component and which is controlled by a computer (microprocessor) executing software that includes an algorithm embodying procedure 1900 encoded or stored on a computer-readable medium. The process shown in FIG. 27 is similar to an analogous process described in detail in Macioszek et al., "Methods for Performing Multi-Formatted assays," U.S. Pat. No. 7,897,337. The steps described represent exemplary TAA procedures only. Persons of ordinary skill will recognize that the steps described below may be varied or omitted or that other steps may be added or substituted in accordance with other real-time amplification assay procedures now known or yet to be developed. Reagent formulations for performing a host of amplification procedures are well known in the art and could be used in or readily adapted for use in the present invention. See, e.g., Kacian et al., U.S. Pat. No. 5,399,491; Becker et al., U.S. Pat. No. 7,374,885; Linnen et al., Compositions and Methods for Detecting West Nile Virus, U.S. Pat. No. 7,115,374; Weisburg et al., "Compositions, Methods and Kits for Determining the Presence of Trichomonas Vaginalis in a Test Sample," U.S. Pat. No. 7,381,811; and Kacian, "Methods for Determining the Presence of SARS Coronavirus in a Sample," U.S. Patent Application Publication No. 2010-0279276 A1.

The process steps of the exemplary real-time TAA amplification assay begin with step 1902, in which a receptacle, such as an MRD 160, is moved to a pipetting position in a sample transfer station (not shown). In step 1904, a sample pipette assembly (not shown) dispenses 100 µL of a target capture reagent ("TCR") including magnetically-responsive particles into the receptacle, e.g., into each receptacle vessel 162 of the MRD 160. The target capture reagent includes a capture probe, a detergent-containing lytic agent, such as lithium lauryl sulfate, for lysing cells and inhibiting the activity of RNAses present in the sample material, and about 40 µg Sera-Mag™ MG-CM Carboxylate Modified (Seradyn, Inc., Indianapolis, Ind.; Cat. No. 24152105-050250), 1 micron, super-paramagnetic particles having a covalently bound poly(dT)14. The capture probe includes a 5' target binding region and a 3' region having a poly(dA)30 tail for binding to the poly(dT)14 bound to the magnetic particle. The target binding region of the capture probe is designed to bind to a region of the target nucleic acid distinct from the regions targeted by the primers and the detection probe.

In step 1906, 400 µL of sample is dispensed into the receptacle. In step 1908, the receptacle, e.g., MRD 160, is moved to a mixer (not shown), and in step 1909, the sample and TCR are mixed, preferably at 16 Hz for 60 seconds. Note that the times given in FIG. 27 and the description thereof are desired times, and the actual times may, in practice, vary from the given desired times.

In one embodiment, the diagnostic analyzer includes three incubators maintained at three different temperatures: a first incubator maintained at 64° C. for target capture and primer annealing, a second incubator maintained at 43.7° C. for pre-heating receptacles, AT binding, and primer binding, and a third incubator maintained at 42.7° C. for amplification. The first, second, and third incubators may be configured the same as incubator 200 described above, although the first and second incubators may omit the signal detectors 400.

In step 1910, the receptacle is moved to the second incubator to pre-heat the receptacle and its contents at a temperature of 43.7° C. for 276 seconds. In other embodiments, the receptacle may be placed in a temperature ramping station (i.e., a temperature-controlled enclosure (not shown) configured to receive and hold one or more receptacles) for the pre-heating step. In step 1912, the receptacle is moved to the first incubator (i.e., target capture ("TC") incubator) where it resides at 64° C. for 1701 seconds for hybridization of the capture probe to target nucleic acids extracted from the sample. (At this temperature, there will be no appreciable hybridization of the capture probe to the immobilized poly(dT)14 oligonucleotide.) In step 1914, the receptacle is moved from the TC incubator to the second incubator for AT binding where it is held for 313 seconds at 43.7° C. to allow for immobilized oligonucleotides associated with the magnetic particles to bind to the capture probes. In step 1916, the receptacle is moved to a cooling chiller (i.e., a temperature-controlled enclosure configured to receive and hold one or more receptacles (not shown)) where the receptacle is held at 18° C. for 481 seconds.

In step 1918, the receptacle is moved to a magnetic parking station (not shown), which is a structure configured to hold one or more receptacles in proximity to one or more magnets so that the contents of each receptacle vessel 162 are exposed to a magnetic field to draw the magnetically-responsive particles of the target capture reagent to a portion of the receptacle adjacent to the magnet and out of suspension. A suitable magnetic parking station is described in Davis, et al., U.S. Patent Application Publication No. 2010/0294047, "Method and System for Performing a Magnetic Separation Procedure."

In step 1920, the receptacle is moved to a magnetic separation station (not shown) for the magnetic separation wash procedure, such as is described in Lair et al., U.S. Patent Application Publication No. 2007-0243600 A1. Within the magnetic separation station, magnets, which are selectively placed in close proximity to the reaction vessel, are used to draw and hold the magnetically-responsive particles to a portion of the vessel. Once the magnetically-responsive particles, and any target nucleic acid bound thereto, are thus immobilized, the hybridized nucleic acid can be separated from non-hybridized nucleic acid by aspirating fluid from the reaction vessel. After the initial aspiration of the fluid contents from the vessel, 1 mL of wash solution is added to the receptacle in step 1922. Step 1924 comprises a second magnetic wash, which includes, after the fluid contents of the receptacle are aspirated, adding 1 mL wash solution to the receptacle in step 1926 and adding 100 µL oil (e.g., silicone oil), or other surface treating agent, to the receptacle in step 1928. In step 1930, a final magnetic wash procedure is performed (in other embodiments, more or fewer magnetic wash procedures can be performed) followed by a final dispense of 100 µL oil (e.g., silicone oil), or other surface treatment agent, in step 1932.

An advantage of adding a surface treating agent, such as silicone oil, to the sample solution in steps 1928 is that it reduces the amount of material that adheres to the inner surfaces of the reaction vessels 162 during the rinsing and aspiration steps of a magnetic separation wash procedure, thereby facilitating a more effective magnetic separation wash procedure. Although the MRDs 160 are preferably made of a hydrophobic material, such as polypropylene, small droplets of material, such as wash solution, may still form on the inner surfaces of the MRD receptacle vessels 162 during the aspiration steps of a magnetic separation wash procedure. If not adequately removed from the receptacle vessels 162 during the magnetic separation wash procedure, this residual material, which may contain nucleic acid amplification inhibitors, could affect assay results. In alternative approaches, the surface treating reagent could be added to the receptacle vessels 162 and removed prior to adding TCR and sample or the surface treating agent could be added to the reaction tubes after TCR and sample have been aspirated from the reaction tubes, possibly with the wash solution, and then removed prior to adding amplification and enzyme reagents to the reaction tubes. The objective is to provide inner surfaces of the receptacle vessels 162 with a coating of the surface treating agent. Inhibitors of amplification reactions are known in the art and depend on the sample source and amplification procedure to being used. Possible amplification inhibitors include the following: hemoglobin from blood samples; hemoglobin, nitrates, crystals and/or beta-human chorionic gonadotropin from urine samples; nucleases; proteases; anionic detergents such as sodium dodecyl sulfate (SDS) and lithium lauryl sulfate (LLS); and EDTA, which is an anticoagulant and fixative of some specimens that binds divalent cations like magnesium, which, as noted above, is a cofactor used in nucleic acid-based amplification reactions. See, e.g., Mahony et al., J. Clin. Microbiol., 36(11):3122-2126 (1998); Al-Soud, J. Clin. Microbiol., 39(2):485-493 (2001); and Kacian et al., "Method for Suppressing Inhibition of Enzyme-Mediated Reactions By Ionic Detergents Using High Concentration of Non-Ionic Detergent," U.S. Pat. No. 5,846,701. Silicone oil is added to each reaction vessel 162 of the MRD 160 in step 1932 to prevent evaporation and splashing of the fluid contents during subsequent manipulations.

In step 1934, amplification reagent, which is stored in a chilled environment, is added to each receptacle while the receptacle is held at 45° C. at an amplification load station (not shown). In step 1936, 75 µL of an amplification reagent are dispensed into the receptacle disposed within the load station, and the receptacle is then mixed for 25 seconds at 16 Hz by a mixer incorporated into the load station. For the exemplary TAA reactions, the amplification reagents contain an antisense promoter-primer having a 3' target binding region and a 5' promoter sequence recognized by an RNA polymerase, a sense primer that binds to an extension product formed with the promoter-primer, nucleoside triphosphates (i.e., dATP, dCTP, dGTP, dTTP, ATP, CTP, GTP and UTP), and cofactors sufficient to perform a TAA reaction. For the real-time TAA amplification assay, the amplification reagent also contains strand displacement, molecular torch probes having interacting label pairs (e.g., interacting fluorescent and quencher moieties joined to the 5' and 3' ends thereof by conventional means) and a target specific region capable of detectably hybridizing to amplification products as the amplification is occurring and, preferably, not to any non-target nucleic acids which may be present in the receptacles. See Kacian et al., U.S. Pat. No. 5,399,491; Becker et al., "Single-Primer Nucleic Acid Amplification," U.S. Pat. No. 7,374,885 (disclosing an alternative TAA-based amplification assay in which an antisense primer and a sense promoter oligonucleotide blocked at its 3' end are employed to minimize side-product formation); and Becker et al., U.S. Pat. No. 6,361,945.

In step 1938, the receptacle is moved to the second incubator and preheated at 43.7° C. for 286 sec. In step 1940, the receptacle is moved to the first incubator and incubated at 64° C. for 636 seconds for primer annealing. In step 1942, the receptacle is moved to the second incubator and incubated for 405 seconds at 43.7° C. for binding of the promoter-primer to a target nucleic acid. The preferred promoter-primer in this particular TAA example has a promoter sequence recognized by a T7 RNA polymerase.

In step 1944, the receptacle is moved to the load station for enzyme reagent addition at 45° C. In step 1946, 25 µL of enzyme are added and the MRD is mixed at 10 Hz for 15 seconds. In step 1948, the receptacle is moved to the third incubator (amplification incubator), where the receptacle contents are incubated at 42.7° C. for 3569 seconds for amplification. During amplification, real-time fluorescence measurements are taken in step 1950. In one embodiment, step 1950 comprises taking multiple, real-time fluorescence measurements during rotation of the carousel 242 whereby each receptacle vessel 162 of each MRD 160 is interrogated by each signal detector 400 once per revolution of the carousel 242. During step 1950, each channel of each signal detector 400 is periodically self-checked, e.g., once every five revolutions of the carousel 242 as described above, using steps 356 to 366 of the automated self-check procedure 350 shown in FIG. 18. The enzyme reagent of this example contains a reverse transcriptase and a T7 RNA polymerase for performing TAA.

After the nucleic acid-based assay is complete, and to avoid possible contamination of subsequent amplification reactions, the reaction mixture can be treated with a deactivating reagent which destroys nucleic acids and related amplification products in the reaction vessel. In such an example, following amplification and real-time measurements, in step 1952, the receptacle is moved to a deactivation queue, or module (not shown), and, in step 1954, 2 mL of a bleach-based agent are provided to each receptacle to deactivate nucleic acid (i.e., alter the nucleic acid such that it is non-amplifiable) present in the receptacle. Such deactivating agents can include oxidants, reductants and reactive chemicals, among others, which modify the primary chemical structure of a nucleic acid. These reagents operate by rendering nucleic acids inert towards an amplification reaction, whether the nucleic acid is RNA or DNA. Examples of such chemical agents include solutions of sodium hypochlorite (bleach), solutions of potassium permanganate, formic acid, hydrazine, dimethyl sulfate and similar compounds. More details of a deactivation protocol can be found in, e.g., Dattagupta et al., U.S. Pat. No. 5,612,200, and Nelson et al., U.S. Patent Application Publication No. US 2005-0202491 A1.

As noted above, the incubator 200 includes a number of signal detectors 400 configured to measure in real time the concentration of unquenched fluorescent dye molecules located in the MRD 160. As discussed above, the assay is designed such that the fluorescent signal increases as the concentration of the target is increased by amplification. The detectors 400, therefore, may be used to monitor the amplification process by monitoring the emergence of the fluorescent signal.

Figure 29:
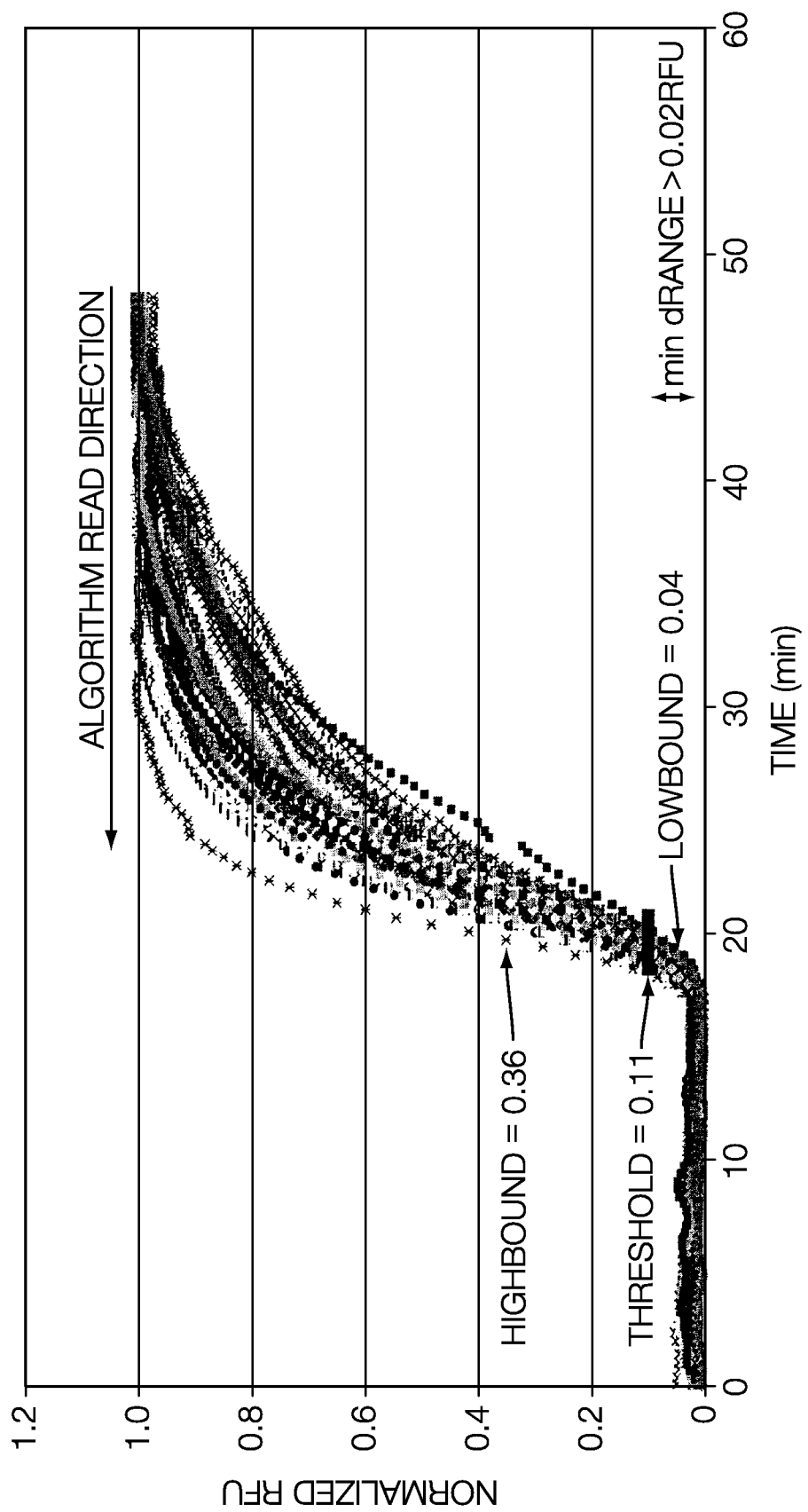
FIG. 29 is a time plot of real-time fluorometer data.

Once the data has been collected by measuring fluorometric emissions from each receptacle at prescribed intervals for a prescribed period of time, and while periodically self-checking the fluorometer as described above to confirm that the fluorometer is functioning properly, the data is processed to determine the concentration of a particular analyte (e.g., target nucleic acid) in the sample. The measured data, that is, the measured signal, will be referred to in terms of a Relative Fluorescent Unit ("RFU"), which is the signal generated by the detection PCB 422 of the signal detector 400 based on the amount of emission fluorescence focused onto the detection element 423. Each data point, measured at a given time interval, is RFU(t). Plots of RFU(t) for a variety of data sets, known as "growth curves" are shown in FIG. 29. In general, each RFU(t) plot is generally sigmoidal in shape, characterized by an initial, flat portion (known as the "static level" or "baseline phase") at or near a minimum level, followed by an abrupt and relatively steeply sloped portion (known as the "growth phase"), and ending with a generally flat portion at or near a maximum level (known as the "plateau phase").

As used herein, a "growth curve" refers to the characteristic pattern of appearance of a synthetic product, such as an amplicon, in a reaction as a function of time or cycle number. A growth curve is conveniently represented as a two-dimensional plot of time (x-axis) against some indicator of product amount, such as a fluorescence measurement—RFU (y-axis). Some, but not all, growth curves have a sigmoid-shape. The "baseline phase" of a growth curve refers to the initial phase of the curve wherein the amount of product (such as an amplicon) increases at a substantially constant rate, this rate being less than the rate of increase characteristic of the growth phase (which may have a log-linear profile) of the growth curve. The baseline phase of a growth curve typically has a very shallow slope, frequently approximating zero. The "growth phase" of a growth curve refers to the portion of the curve wherein the measurable product substantially increases with time. Transition from the baseline phase into the growth phase in a typical nucleic acid amplification reaction is characterized by the appearance of amplicon at a rate that increases with time. Transition from the growth phase to the plateau phase of the growth curve begins at an inflection point where the rate of amplicon appearance begins to decrease. The "plateau phase" refers to the final phase of the curve. In the plateau phase, the rate of measurable product formation is substantially lower than the rate of amplicon production in the log-linear growth phase, and may even approach zero.

Figure 28:
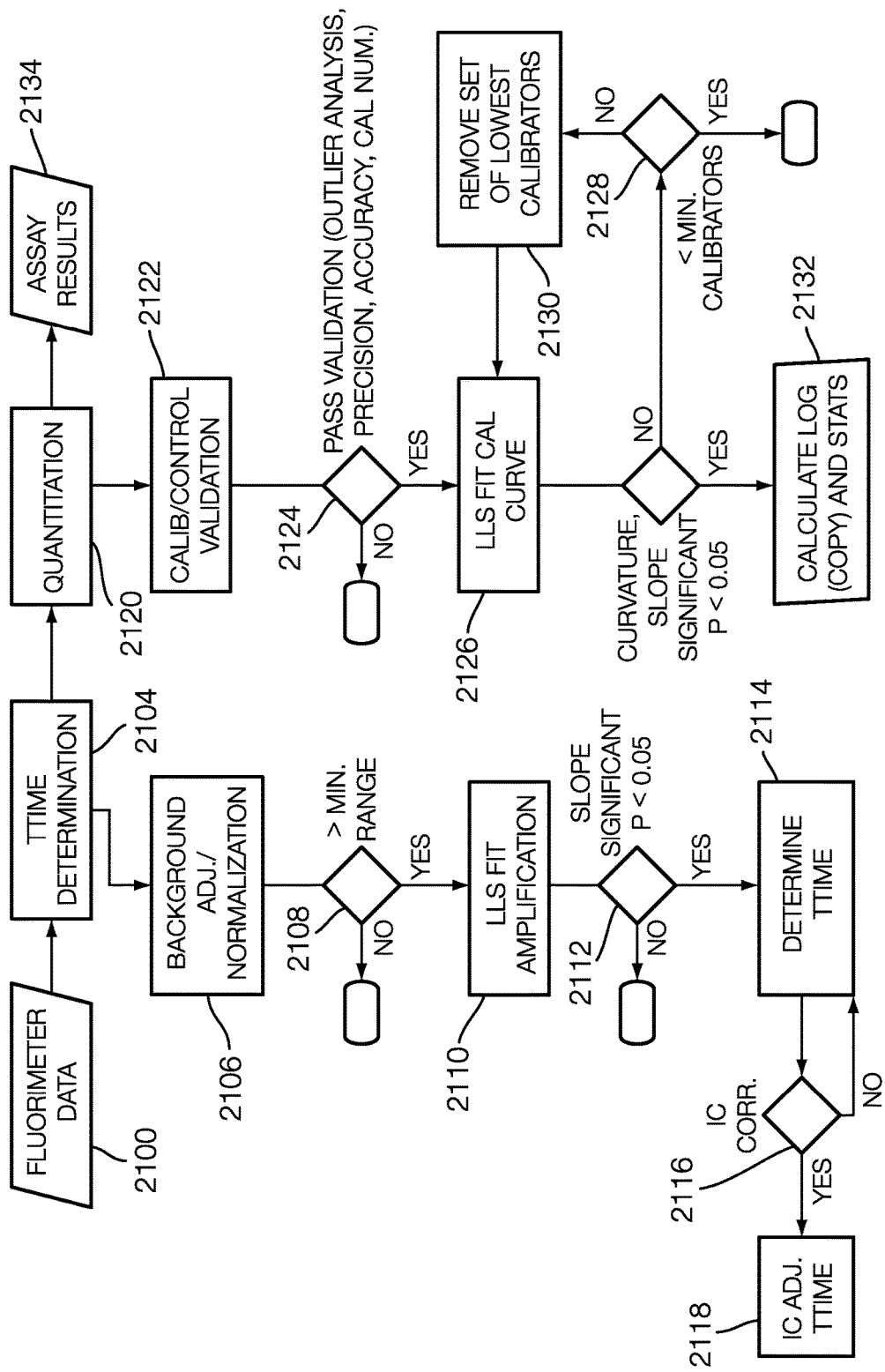
FIG. 28 is a flow chart showing an analyte quantification process.

A process for calculating an analyte concentration is shown by means of a flow chart in FIG. 28. The RFU(t) data from the signal detector 400 is input as represented at box 2100. The RFU(t) data goes to threshold time determination, which begins at 2104. Threshold time, or T-time, (also known as time of emergence) refers to the time at which the data RFU(t), normalized as discussed below, reaches a predefined threshold value. Using calibration curves, as will be described in more detail below, the T-time determined for a particular sample can be correlated with an analyte concentration, thereby indicating the analyte concentration for the sample. In general, the higher the concentration of the analyte of interest, the sooner the T-time is reached.

The first step of the T-time determination procedure is background adjustment and normalization of the data, as represented at box 2106. Background adjustment is performed to subtract that portion of the signal data RFU(t) that is due to background "noise" from, for example, stray electromagnetic signals. That is, the background noise includes that part of the RFU(t) signal due to sources other than the analyte of interest. Background adjustment is performed by subtracting a background value "BG" from the data RFU(t) to obtain adjusted data RFU*(t). That is, RFU*(t)=RFU(t)−BG.

The background BG can be determined in a number of ways.

In accordance with one method for determining the background noise, the first step is to determine the time intervals between data points. The time interval is determined by multiplying cycle time (i.e., the time between consecutive data measurements) by the data point (i.e., $0^{th}$ data point, $1^{st}$ data point, $2^{nd}$ data point, . . . , $n^{th}$ data point) and divide by 60 seconds. For example, assuming a cycle time of 30 seconds, the time interval for the $15^{th}$ data point is (15×30 sec.)/60 sec.=7.5.

The next step is to find the midpoint of the signal data by adding the minimum signal data point and the maximum signal data point and dividing by two. That is:

$(RFU_{max}+RFU_{min})/2.$

Starting at the time corresponding to the midpoint value and working backwards, calculate the slope for each pair of data points: (RFU(t) RFU(t−1))/Δt (t→t−1).

Next, determine where the slope of RFU(t) flattens out by finding the first slope value that is less than the static slope value (i.e., the value before the RFU(t) curve begins its upward slope). A representative static slope value, also known as the "delta value," includes 0.0001. Once this slope is found, find the next cycle in which the slope that is not negative or is, for example, above the negative delta value (i.e., −0.0001); this value is $H_{index}$. Next, take the mean of the entire range of RFU(t) values starting at the first data point and go to the RFU value that corresponds to the $H_{index}$ value. The mean of this data may be computed using the Excel TRIMMEAN function on this range of data using a static back trim value of 0.15 (that is, the lowest 7.5% of RFU values in the specified range and the highest 7.5% RFU values in the specified range are excluded). This mean value is the background, BG. Alternatively, the background can be determined in accordance with the procedure described above using a delta value other than 0.0001.

A further alternative method for determining the background eliminates the delta value criterion and instead take a TRIMMEAN mean of the RFU data from cycle 1 to a prescribed end point, such as the first cycle before 5.5 minutes. For this alternative, the static back trim value may be adjusted to, for example, 0.40 (that is, the lowest 20% of RFU values in the specified range and the highest 20% RFU values in the specified range are excluded from the background calculation).

A further alternative method for determining the background is to perform a curve fit on all or a portion of the RFU data to derive an estimate of the baseline value, which is the background to be subtracted. Any curve fit technique suitable for fitting a curve to the RFU data can be used.

An exemplary curve fit technique is to use a portion of the equation derived by Weusten et al. for curve fit of the typically sigmoidal curves associated with nucleic acid amplification. See Weusten et al., Nucleic Acids Research, 30(6e26):1-7 (2002). For background subtraction, it is only necessary to ascertain the baseline level. Thus, it is also only necessary to fit a curve to the first portion of the RFU data encompassing the baseline, usually toward the beginning of the curve.

The curve fit may be performed on the RFU(t) data from cycle 1 to the cycle just before 75% of the maximum RFU. The following polynomial equation (3), which, as mentioned above, is a portion of the equation derived by Weusten et al, is used to generate a best fit model of the RFU data:

$$RFU(t) = Y0 + a1 a2 [e^{a2(t-a3)}/(1+e^{a2(t-a3)})] \ln(1+e^{a2(t-a3)}) \quad (3)$$

Initial estimates for the variables Y0, a1, a2, and a3, as discussed below, are input to the curve-fit equation and an iterative solution fitting the equation to the RFU data is performed, for example, using the SOLVER function of Microsoft EXCEL, to yield the final equation and the final values for Y0, a1, a2, and a3.

Y0 = is the baseline; an initial value can be RFU(1).

a1 = relates to the steep portion (growth phase) of the RFU(t) data; 0.05 can be a suitable initial estimate for a1.

a2 = relates to the steep portion (growth phase) of the RFU(t) data; 1.0 can be a suitable initial estimate for a2.

a3 = relates to the transition between the baseline and the slope feature; the time, or cycle, at which RFU(t) reaches a value just before 25% of $RFU_{max}$ is a suitable initial estimate for a3.

When the final values of Y0, a1, a2, and a3 have been derived, Y0 is treated as the back ground, and is subtracted from the RFU(t) data for which the curve fit was performed.

Curve fit equations other than that described above can be used. For example, the commercially available TABLE-CURVE software package (SYSTAT Software Inc.; Richmond, Calif.) can be used to identify and select equations that describe exemplary real-time nucleic acid amplification curves. One such exemplary resulting equation, used for mathematical modeling, is given by equation (4):

$$RFU(t) = Y0 + b(1-\exp(-(t-d^*\ln(1-2^{-(-1/e)})-c)/d))^{-e} \quad (4)$$

Still another exemplary resulting equation is given by equation (5):

$$RFU(t) = Y0 + b/(1+\exp(-(t-d^*\ln(2^{-(-1/e)}-1)-c)/d))^{-e} \quad (4)$$

In each case, as described above, the equation can be solved, for example, using the SOLVER function of Microsoft EXCEL, to yield the final equation and the final values for Y0 and the other parameters, and the solutions yields a Y0 that is the background to be subtracted from the RFU(t) data.

To normalize the data, each data point, adjusted for the background, is divided by the maximum data point, also adjusted for the background. That is:

$$\text{Normalized } RFU = RFU_n(t) = \frac{RFU^*(t)}{RFU^*_{max}} = \frac{(RFU(t) - BG)}{(RFU_{max} - BG)}$$

Thus, the $RFU_n(t)$ will be from −1 to 1.

In step 2108, the range of data is calculated by subtracting $RFU_{n(min)}$ from $RFU_{n(max)}$. If the calculated range does not meet or exceed a specified, minimum range (e.g., 0.05), the data is considered suspect and of questionable reliability, and, thus, the T-time will not be calculated. The minimum range is determined empirically and may vary from one fluorescence measuring instrument to the next. Ideally, the specified minimum range is selected to ensure that the variation of data values from minimum to maximum exceeds the noise of the system.

In step 2110, a curve fit procedure is applied to the normalized, background-adjusted data. Although any of the well-known curve fit methodologies may be employed, in a preferred embodiment, a linear least squares ("LLS") curve fit is employed. The curve fit is performed for only a portion of the data between a predetermined low bound and high bound. The ultimate goal, after finding the curve that fits the data, is to find the time corresponding to the point at which the curve intersects a predefined threshold value. In the preferred embodiment, the threshold for normalized data is 0.11. The high and low bounds are determined empirically by fitting curves to a variety of control data sets and observing the time at which the various curves cross the chosen threshold. The high and low bounds define the upper and lower ends, respectively, of the range of data over which the curves exhibit the least variability in the times at which the curves cross the given threshold value. In the preferred embodiment, the low bound is 0.04 and the high bound is 0.36—See FIG. 29. The curve is fit for data extending from the first data point below the low bound through the first data point past the high bound.

At step 2112, determine whether the slope of the fit is statistically significant. For example, if the p value of the first order coefficient is less than 0.05, the fit is considered significant, and processing continues. If not, processing stops. Alternatively, the validity of the data can be determined by the R2 value.

The slope m and intercept b of the linear curve y=mx+b are determined for the fitted curve. With that information, T-time can be determined at step 2114 as follows:

$$T\text{-time} = \frac{\text{Threshold} - b}{m}$$

Figure 30:
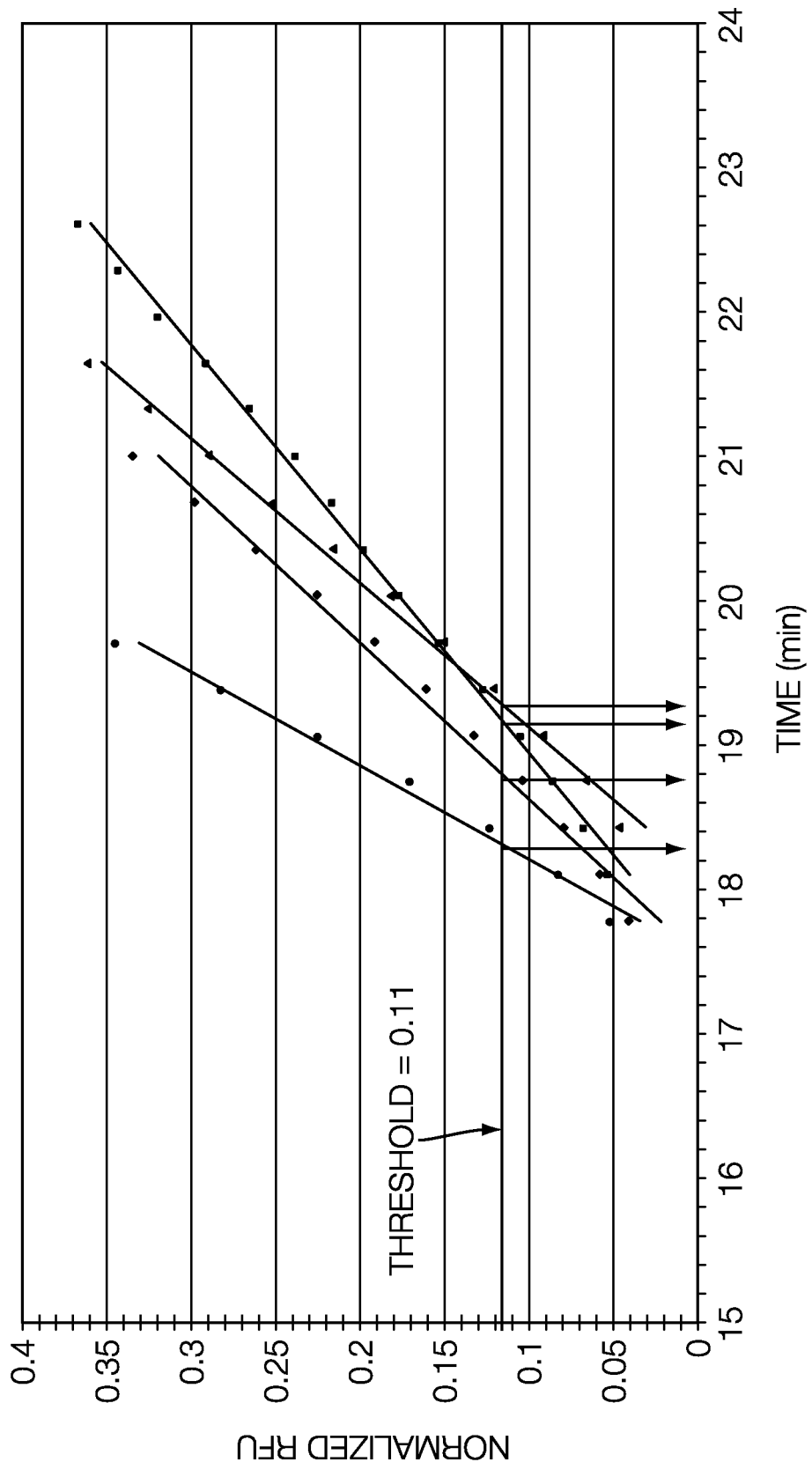
FIG. 30 is a plot showing a method for fitting a curve to real-time fluorometer data and using the fit to determine a threshold time.

The technique of using the fitted curve to determine T-times is illustrated graphically in FIG. 30.

Returning to FIG. 28, at step 2116, it is determined whether or not internal control/calibrator adjustments are desired. Typically, a test procedure would include at least one reaction vessel with a known concentration of a nucleic acid (other than a nucleic acid of interest) as a control, or, alternatively, a control nucleic acid sequence can be added to each sample. The known concentration can be simply used as control to confirm that a reaction did take place in the reaction vessel. That is, if the known concentration is amplified as expected, successful reaction is confirmed and a negative result with respect to the target analyte is concluded to be due to absence of target in the sample. On the other hand, failure to amplify the known concentration as expected indicates a failure of the reaction and any result with respect to the target is ignored.

The known concentration can be used to calibrate the concentration of the target at step 2118. The T-times corresponding to a series of standards containing internal control and target sequences are determined for a statistically valid number of data sets. Using this data, a calibration plot is constructed from which the test sample's concentration is interpolated as described below.

One method of constructing the calibration plot places the known concentrations of target analyte on the x-axis versus the difference between target and control T-times on the y-axis. Subsequently, the test sample's concentration is interpolated from the calibration curve fit. Another method of constructing the calibration plot places the known concentration of target analyte on the x-axis versus the fraction [target T-time/internal control T-time] on the y-axis. Subsequently, the test sample's concentration is interpolated from the calibration curve fit. An example of this is disclosed in Haaland, et al., "Methods, Apparatus and Computer Program Products for Determining Quantities of Nucleic Acid Sequences in Samples Using Standard Curves and Amplification Ratio Estimates," U.S. Pat. No. 6,066,458. A further alternative method of constructing the calibration plot utilizes a parametric calibration method, such as the method described in Carrick et al., "Parametric Calibration Method," U.S. Pat. No. 7,831,417.

Occasionally, data sets exhibit a dip just after the initial static baseline (i.e., the initial, flat part of the RFU(t) curve, see FIG. 29) and just before the data begins its upward slope. To identify and correct such data, and prior to determining the T-time for that data, the following algorithm is employed. Starting at $H_{index}$, check each RFU(t) value to determine if it is less than the background value, BG. If yes, subtract RFU(t) from BG (the result should be a positive number). This will be the CorValue. Add the CorValue to the background subtracted value, this in turn will bring RFU(t) up to the baseline. Perform this analysis working forward on each RFU(t) value until the latest CorValue is less than the preceding CorValue. Add the greatest CorValue to each of the remaining background subtracted RFU(t) values. Now, the corrected data set can be normalized and the T-time determined as described above.

If a curve fit method is used to derive the background level, it may not be necessary to perform the dip correction described above. It may also be desirable to perform outlier detection on the data set to identify and, if necessary, discard data points that exhibit abnormal values as compared to the remaining data points. Any of the well-known outlier detection methodologies can be used.

The quantitation procedure 2120 is the second part of the analyte concentration determination. T-times are determined for known concentrations of analytes for known conditions. Using this data, relationships between analyte concentrations (typically expressed as log copy) and T-times can be derived. After a T-time is determined for a particular sample, the derived relationship (Log copy=f (T-time)) can be used to determine the analyte concentration for the sample.

More specifically, at steps 2122 and 2124, calibration/control data sets for a control analyte of known concentrations are validated by, for example, outlier analysis and/or any other known data validation methodologies. If the data is found to be valid, calibration continues, otherwise, calibration stops.

T-times for the control data sets are determined, and T-time vs. Log copy is plotted for all samples of a particular condition (e.g., samples processed with reagents from a particular batch lot). In step 2126, a curve fit, such as a linear least squares fit, is performed on a portion of the T-time vs. Log copy plot to find the slope m and intercept b of the line that best fits the data. If the number of available T-time vs. Log copy data points (known as "calibrators") is not less than a predefined minimum number of calibrators (as determined at step 2128), lowest calibrators, if any, are removed at step 2130, as follows:

After finding the best fit line for the calibrator data points, $2^{nd}$ and $3^{rd}$ order curve fits are tested as well. If these fits are significantly better than the $1^{st}$ order, linear fit, the calibrator data point that is furthest from the linear curve fit is discarded, and $1^{st}$, $2^{nd}$, and $3^{rd}$ fits are found and compared again with the remaining calibrators. This process is repeated—assuming that the number of calibrators is not less than the minimum acceptable number of calibrators—until the 2nd and 3rd order fits are not significantly better than the $1^{st}$ order, linear fit.

When the linear T-time vs. Log copy equation has been derived, the concentration (as Log copy) of the analyte of interest for a sample is determined, at step 2132, by plugging the T-time for that sample into the equation. Thus, the assay results are obtained 2134.

All documents referred to herein are hereby incorporated by reference herein. No document, however, is admitted to be prior art to the claimed subject matter.

While the invention has been described in connection with what are presently considered to be the most practical and preferred embodiments, it is to be understood that the invention is not to be limited to the disclosed embodiments, but, on the contrary, is intended to cover various modifications and equivalent arrangements included within the spirit and scope of the appended claims.

Furthermore, those of the appended claims which do not include language in the "means for performing a specified function" format permitted under 35 U.S.C. §112(å6), are not intended to be interpreted under 35 U.S.C. §112(¶6) as being limited to the structure, material, or acts described in the present specification and their equivalents.

The invention claimed is:

1. A system for monitoring the performance of a fluorometer in a dynamic environment, comprising
   a fluorometer comprising two or more channels, each channel having a separate light source, optical focus and filter assembly, and optical signal detector, and wherein each channel is configured to focus the light source at a detection zone;
   a support comprising two or more fluorescent reference standards, each fluorescent reference standard corresponding to a single channel of the fluorometer, wherein the support is arranged to accommodate two or more removable receptacle vessels; and
   a drive mechanism configured to adjust the relative horizontal positioning between the reference standards and the fluorometer such that each of the two or more fluorescent reference standards can be positioned in or out of optical communication with its corresponding channel of the fluorometer.

2. The system of claim 1, wherein the fluorescent reference standard is positioned in optical communication with the corresponding channel of the fluorometer, and wherein the fluorescent reference standard is out of focus relative to the detection zone.

3. The system of claim 1, wherein the two or more fluorescent reference standards are positioned in a linear arrangement on the support.

4. The system of claim 3, wherein at least one of the fluorescent reference standards in the linear arrangement has emission characteristics that differ from at least one of the other fluorescent reference standards in the linear arrangement.

5. The system of claim 1, wherein only one of the fluorescent reference standards can be positioned in optical communication with one of the two or more channels of the fluorometer at a time.

6. The system of claim 2, wherein the fluorescent reference standard is positioned between about 1% to 99% closer to the corresponding channel relative to the detection zone.

7. The system of claim 2, wherein the fluorescent reference standard is positioned at the same distance from its corresponding channel as the distance between the channel and the detection zone.

8. The system of claim 2, wherein the fluorescent reference standard is positioned between about 1% to 99% farther from its corresponding channel relative to the detection zone.

9. The system of claim 1, wherein the fluorometer is stationary, and the drive mechanism is configured to adjust the relative horizontal positioning between the reference standards and the fluorometer by adjusting the horizontal positioning of the support.

10. The system of claim 1, wherein the support comprises a rotatable carousel, and wherein the fluorometer is fixed with respect to the carousel and the drive mechanism is configured to adjust the relative horizontal positioning between the reference standards and the fluorometer by effecting angular movement of the carousel around a central axis.

11. The system of claim 1, wherein the system comprises two or more fluorometers, each fluorometer comprising two or more channels, each channel having a separate light source, optical focus and filter assembly, and optical signal detector, and wherein each channel is configured to focus the light source at a detection zone.

12. The system of claim 11, wherein each fluorometer has a different light source, optical focus and filter assembly, and optical signal detector, such that each fluorometer emits a different excitation signal and detects a different emission signal.

* * * * *